US008247432B2

(12) United States Patent
Breslin et al.

(10) Patent No.: US 8,247,432 B2
(45) Date of Patent: *Aug. 21, 2012

(54) TRIPEPTIDYL PEPTIDASE INHIBITORS

(75) Inventors: Henry Joseph Breslin, Lansdale, NJ (US); Hans Louis Jos De Winter, Schilde (BE); Michael Joseph Kukla, Maple Glen, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/111,010

(22) Filed: May 19, 2011

(65) Prior Publication Data

US 2011/0224255 A1    Sep. 15, 2011

Related U.S. Application Data

(60) Continuation of application No. 11/928,273, filed on Oct. 30, 2007, now Pat. No. 7,947,713, which is a continuation of application No. 11/499,937, filed on Aug. 7, 2006, now abandoned, which is a division of application No. 10/415,623, filed as application No. PCT/EP01/12388 on Oct. 24, 2001, now Pat. No. 7,125,891.

(60) Provisional application No. 60/244,223, filed on Oct. 30, 2000.

(51) Int. Cl.
*A61K 31/4709* (2006.01)
*A61K 31/4178* (2006.01)
*A61K 31/422* (2006.01)
*A61P 25/00* (2006.01)
*C07D 401/04* (2006.01)
*C07D 233/54* (2006.01)
*C07D 271/08* (2006.01)

(52) U.S. Cl. ........ 514/314; 514/397; 514/374; 546/167; 548/311.4; 548/125

(58) Field of Classification Search .................. None
See application file for complete search history.

(56) References Cited

U.S. PATENT DOCUMENTS

| 3,023,235 | A | 2/1962 | Frederick |
| 3,769,218 | A | 10/1973 | Hohenlohe et al. |
| 4,563,306 | A | 1/1986 | Ishida et al. |
| 5,610,144 | A | 3/1997 | Capet et al. |
| 6,403,561 | B1 | 6/2002 | Rose et al. |
| 7,125,891 | B2 * | 10/2006 | Breslin et al. ............... 514/307 |
| 7,947,713 | B2 | 5/2011 | Breslin et al. |
| 2002/0161189 | A1 | 10/2002 | Lazarus et al. |
| 2003/0027743 | A1 | 2/2003 | Rose et al. |
| 2006/0276509 | A1 | 12/2006 | Breslin et al. |

FOREIGN PATENT DOCUMENTS

| EP | 198264 | 3/1986 |
| EP | 506468 | 9/1992 |
| FR | 2735776 A1 | 12/1996 |
| JP | 5339240 | 6/1905 |
| WO | WO 93/01167 | 1/1993 |
| WO | WO 96/06855 | 3/1996 |
| WO | WO 96/35805 A1 | 11/1996 |
| WO | WO 98/40400 | 9/1998 |
| WO | WO 99/33801 | 7/1999 |
| WO | WO 99/55679 A1 | 11/1999 |
| WO | WO 99/62879 | 12/1999 |
| WO | WO 02/63116 | 5/2002 |

OTHER PUBLICATIONS

International Search Report relating to International Patent Application No. PCT/EP01/12388, filed Oct. 15, 2009. Date of Mailing of International Search Report: Jun. 28,2002.
Smith G.P. et al., J. Ann. N. Y. Acad. Sci., 1994, pp. 236-241, 713.
Woodruff G. et al., Rev. Pharmac., 1991, pp. 469-501, vol. 31.
Smith G.P. et al., Am. J. Physiol., 1985, pp. R638-R641, vol. 249.
Rose C. et al., Nature, 1996, pp. 403-409, vol. 380.
Munson, P.J. and Rodbard, D., Anal. Biochem. 107: 220-239, 1980.
Fulhage et al., caplus an 1959:89388.
Bedoya et al., caplus an 1997;302763.
Merriam-Webster Online Dictionary; http://www.merriam-webster.com/dictionary/residue, (2011).
Aldrich J. V., Analgesics, Burgers' Medicinal Chemistry and Drug Discovery, 5th Edition, vol. 3, Therapeutic Agents, John Wiley & sons, Inc. 1996, pp. 321-441.
Balboni G., et al., Evaluation of the Dmt-Tic Pharmaceophore: Conversion of a Potent -Opioid Receptor Antagonist into a Potent Agonist and Ligands with Mixed Properties, J. Med. Chem., 2002, 45, pp. 713-720.
Balboni G., et al., Opioid pseudopeptides containing heteroaromatic or heteroaliphatic nuclei, Peptides 2000, 21, pp. 1663-1671.
Berge S.M., et al., Pharmaceutical Salts, Journal of Pharmaceutical Sciences, 1977, Jan, vol. 66, No. 1, pp. 1-19.
Borg S., et al., Synthesis of 1,2,4-Oxadiazole-, 1,3,4-Oxadiazole, and 1,2,4-Triazole-Derived Dipeptidomimetrics, Journal of Organic Chemistry, American Chemical Society, Easton, US, vol. 60, No. 10, May 19, 1995, pp. 3112-3120, XP000973994, ISSN:0022-3263.
Database Biosis 'Online! Biosciences Information Service, Philadelphia, PA, US, 1976, Wuonola M.A. et al., Imidazole Alkaloids of Macrorungia-Longistrobus Revised Structures and total Syntheses, Database accession No. PREV197662056525, XP002199740 abstract. Dondoni A., et al. Addition of 2-silylazoles to heteroaryl cations, synthesis of unsymmetrical azadiaryls, Tetrahedron Letters, Elsevier Science Publishers, Amsterdam, NL vol. 25, No. 33, 1984, pp. 3637-3640, XP002138665.
Fries, D.S., Analgesics, Principles of Medicinal Chemistry, 4th Ed; W.O. Foye, T.L. Lemke, and D.A. Williams, Eds, Williams and Wilkins, Baltimore, Md. 1995, pp. 247-269.
Fuhlhage et al., Studies on the Formation and Reactions of 1-Pyrroline 1, Journal of American Chem. Soc., 1958, pp. 6249-6254.
Gould P.L., Salt selection for basic drugs, International Journal of Pharmaceutics, vol. 33, 1986, pp. 201-217.
Hoitink M.A., et al., Degradation of Azaglycinamido Residues in Model Tripeptides Derived from Goserelin, Journal of Pharmaceutical Sciences, vol. 89, No. 1, Jan. 2000, pp. 108-114.
Kikuchi K., et al., Syntheses and Structure-Activity Relationships of 5,6,7,8-Tetrahydro-5,5,8,8-tetramethyl-2-quinoxaline Derivatives with Retinoic Acid Receptor a Agonistic Activity, Journal of Medicinal Chemistry, 2000, vol. 43, No. 3, pp. 409-419.

(Continued)

*Primary Examiner* — Yong Chu

(57) ABSTRACT

The present invention is concerned with novel compounds of formula (I) which are inhibitors of a membrane tripeptidyl peptidase responsible for the inactivation of endogenous neuropeptides such as cholecystokinis (CCKs).

8 Claims, No Drawings

OTHER PUBLICATIONS

Krenitsky P.J., et al., Preparation of the 14-membered 1,1-cyloisodityrosine subunit of RP 66453, Tetrahedron Letters, Elsevier Science Publishers, Amsterdam, NL vol. 43, No. 3, Jan. 14, 2002, pp. 407-410, XP004329390.

Leonard, F., Unnatural amino acids. II. Congeners of DL-3-carboxy-4-methoxyphonylalanine. J. Med. Chem. vol. 10, 1967, pp. 478-481, XP 00258212.

Maeda H., et al., Synthesis and Central Nervous System Actions of Thyrotropin-Releasing Hormone Analogs Containing a 1-Oxo-1,2,3,4-tetrahydroisoquinoline Moiety 1, Chem. Pharm, Bull. 36(1)1988, pp. 190-201.

Marsden B. J., et al., Spontaneous degradation via diketopiperazine formation of peptides containing a tetrahydroisoquinoline-3-carboxylic acid residue in the 2—position of the peptide sequence, Int. J. Pept. Protein Res. 1993, 41(3) pp. 313-316.

Obase H., et al., New Antihypertensive Agents II. Studies on New Analog of 4-Piperidylbenzimidazolinones, Chemical and Pharmaceutical Bulletin, Pharmaceutical Society of Japan, Tokyo, Up. vol. 30, No. 2, 1982, pp. 474-483, XP000974108.

Rapoport H., et al., 2,2-Bipyrrole, Journal of the American Society, vol. 84, 1962, pp. 2178-2181.

Riviere et al., Opioid receptors: Targets for new gastrointestinal drug development, Drug Development 2000, pp. 203-238.

Rose C., et al., Characterization and Inhibition of a Cholecystokinin-Inactivating Serine Peptidase, Nature, MacMillan Journals, Ltd. London, GB, vol. 380, No. 6573, Apr. 4, 1996 pp. 403-409. XP002068304.

Salvadori S., et al., Evolution of the Dmt-Tic Pharmacophonre: n-Terminal Methylated Derivatives with Extraordinary Opioid Antagonist Activity, J. Med. Chem, 1997, 40, pp. 3100-3108.

Stanchev M., et al., Synthesis and Antimicrobial Activity in Vitro of New Amino Acids and Peptides Containing Thiazole and Oxazole Moieties, Arch. Pharm. Med. Chem., 1999, pp. 297-304.

Tao Ye et al. Synthesis of Chiral N-Protected a-Amino-b-Diketones from a-Diazoketones Derived from Natural Amino Acids, Tetrahedron 1992, vol. 48, No. 37, pp. 8007-8022.

Tripp et al., Synthesis of methylene-and carbonyl-bridged analogs of iodothyronines and iodothyroacetic acids, Journal of Medicinal Chemistry, American Chemcial Society, Washington, U.S. vol. 16, No. 1 1973, pp. 60-64, XP002113321.

Wentland M.P., et al., 3-Carboxamido Analogues of Morphine and Naltrexone: Synthesis and Opioid Receptor Binding Properties, Biorganic & Medicinal Chemistry Letterss, 2001, (11) pp. 1717-1721.

Wentland M.P., et al., 8-Carboxamidocyclazocine Analogues: Redefiningg the Structure-Activity Relationships of 2,6-Methano-3-benzazocines, Biorganic & Medicinal Chemistry Letters, 2001, (11)pp. 623-626.

Wipf P., et al, Total Synthesis of (-)Muscoride A, Journal of Organic Chemistry, American Chemical Society, Easton, US, vol. 61, 1996, pp. 6517-6522, XP002199739, ISSN:0022-3263.

Wuonola M., et al., Imidazole Alkaloids of Macrorungia Longistrobus Revised Structures and Total Syntheses, Tetrahedron, vol. 32, 1976, pp. 1085-1095.

Database Crossfire Beilstein 'Online! Beilstein Institut zur Foerderung Der Wissenschaften, Frankfurt, DE BRN 524173, XP002199742 abstract, Nov. 28, 1998.

Database Crossfire Beilstein 'Online! Beilstein Institut zur Foerderung Der Wissenschaften, Frankfurt, DE, BRN 165639, XP002199743 abstract, Jun. 27, 1988.

Database Crossfire Beilstein 'Online! Beilstein Institut zur Foerderung Der Wissenschaften, Frankfurt, DE, BRN 543350 XP002199741 abstract, Nov. 28, 1988.

Database Crossfire Beilstein 'Online! Beilstein Institut zur Foerderung Der Wissenschaften, Frankfurt, DE, BRN 8335691, 8332147, XP002199744 abstract, Mar. 7, 2000.

U.S. Office Action relating to abandoned U.S. Appl. No. 11/499,937, issued Dec. 7, 2007.

Final U.S. Office Action relating to abandoned U.S. Appl. No. 11/499,937, issued Jun. 30, 2008.

U.S. Office Action relating to abandoned U.S. Appl. No. 11/499,937, issued Jan. 29, 2009.

Final U.S. Office Action relating to abandoned U.S. Appl. No. 11/499,937, issued Jul. 31, 2009.

U.S. Office Action relating to abandoned U.S. Appl. No. 11/499,937, issued Sep. 27, 2009.

U.S. Office Action relating to abandoned U.S. Appl. No. 11/499,937, issued Jun. 15, 2010.

Final U.S. Office Action relating to abandoned U.S. Appl. No. 11/499,937, issued Dec. 21, 2010.

* cited by examiner

TRIPEPTIDYL PEPTIDASE INHIBITORS

This application is a continuation of U.S. patent application Ser. No. 11/928,273, filed Oct. 30, 2007, now U.S. Pat. No. 7,947,713 which is a continuation of U.S. patent application Ser. No. 11/499,937, filed Aug. 7, 2006, now abandoned which is a divisional application of U.S. patent application Ser. No. 10/415,623, filed Apr. 29, 2003, now U.S. Pat. No. 7,125,891, which is the national stage of PCT Application No. PCT/EP01/12388, filed Oct. 24, 2001 which application claims priority from U.S. Provisional Patent Application Ser. No. 60/244,223, filed Oct. 30, 2000. The disclosures of the U.S. patent applications are hereby incorporated by reference in their entireties.

The present invention is concerned with novel compounds of formula (I) which are inhibitors of a membrane tripeptidyl peptidase responsible for the inactivation of endogenous neuropeptides such as cholecystokinins (CCKs). The invention further relates to methods for preparing such compounds, pharmaceutical compositions comprising said compounds as well as the use as a medicine of said compounds.

Cholecystokinins (CCKs) are a family of hormonal and neuronal peptides which exert pleiotropic biological effects in the gut and brain. The actions of CCK are mediated by $CCK_A$ and $CCK_B$ receptors. CCK is known to have a physiological role in the control of food intake, which is enhanced by $CCK_A$ agonists (Smith G. P. et al., *J. Ann. N.Y. Acad. Sci.*, 713, 236-241 (1994)), and the control of anxiety, which is decreased by $CCK_B$ antagonists (Woodruff G. et al., *Rev. Pharmac.*, 31, 469-501 (1991)).

Tripeptidyl peptidase II (TPP II) is a CCK inactivating peptidase. TPP II is found in neurons responding to cholecystokinin as well as in non-neuronal cells. TPP II is considered to be a neuropeptidase responsible for CCK-8 inactivation (Rose C. et al., *Nature*, 380, 403-409, (1996)).

TPP II could be involved in CCK-8 inactivation in the gastrointestinal tract. Exogenous CCK reduces food intake and elicits other behavioural concomitants of satiation. Food intake is increased by systemic administration of $CCK_A$ receptor agonists (Smith G. P. et al., *J. Ann. N.Y. Acad. Sci.*, 713, 236-241 (1994)). Endogenous CCK-controlling food intake seems to be of neuronal rather than hormonal origin and acts upon peripheral $CCK_A$ receptors on vagal afferent fibres (Smith G. P. et al., *Am. J. Physiol.*, 249, R638-R641 (1985)).

Inhibitors of TPP II are useful tools in investigating the functions of CCK neurons and may be useful drugs for the treatment of disorders such as over-eating, obesity, problems with gastrointestinal motility and psychotic syndromes.

WO-96/35805, published 14 Nov. 1996, discloses inhibitors of a membrane tripeptidylpeptidase responsible for the inactivation of endogenous neuropeptides useful in treatment of gastrointestinal and mental disorders. WO-99/33801, published 8 Jul. 1999, discloses CCK-inactivating tripeptidyl peptidase (TPP II) inhibiting compounds useful in the treatment of eating disorders, obesity, psychotic syndromes and associated psychiatric disorders.

The compounds of the present invention differ from the cited art-known compounds structurally, by the nature of the $R^2$ substituent.

The present invention concerns compounds of formula (I)

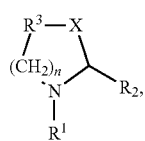
(I)

a stereochemically isomeric form thereof, or a pharmaceutically acceptable addition salt thereof, wherein n is an integer 0 or 1;

X represents O; S; or $-(CR^4R^5)_m-$ wherein m is an integer 1 or 2; $R^4$ and $R^5$ are each independently from each other hydrogen or $C_{1-4}$alkyl;

$R^1$ is $C_{1-6}$alkylcarbonyl optionally substituted with hydroxy; $C_{1-6}$alkyloxycarbonyl; amino$C_{1-6}$alkylcarbonyl wherein the $C_{1-6}$alkyl group is optionally substituted with $C_{3-6}$cycloalkyl; mono- and di($C_{1-4}$alkyl)amino$C_{1-6}$alkylcarbonyl; aminocarbonyl substituted with aryl; $C_{1-6}$alkylcarbonyloxy$C_{1-6}$alkylcarbonyl; $C_{1-6}$alkyloxycarbonylamino$C_{1-6}$alkylcarbonyl wherein the amino group is optionally substituted with $C_{1-6}$alkyl; an amino acid residue bound via the carbonyl group; $C_{1-6}$alkyl substituted with amino; or arylcarbonyl;

$R^2$ is a 5-membered heterocycle selected from

(a-1)

(a-2)

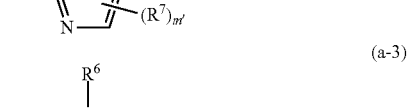
(a-3)

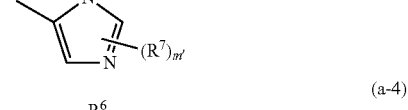
(a-4)

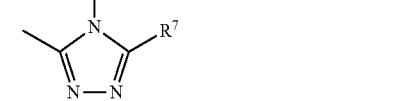
(a-5)

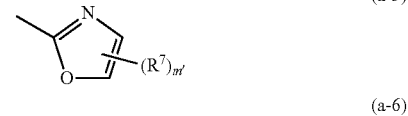
(a-6)

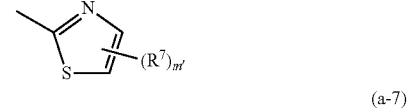
(a-7)

wherein m' is an integer 1 to 2;

$R^6$ is hydrogen or $C_{1-4}$alkyl;

$R^7$ is independently from each other hydrogen; halo; amino; hydroxy; trifluoromethyl; $C_{1-6}$alkyl; $C_{1-4}$alkyl substituted with hydroxy, hydroxycarbonyl, $C_{1-4}$alkyloxycarbonyl, aminocarbonyl, mono- or di($C_{1-4}$alkyl)aminocarbonyl, amino, or mono- or di($C_{1-4}$alkyl)amino; phenyl; aminocarbonyl; hydroxycarbonyl; $C_{1-4}$alkyloxycarbonyl; $C_{1-4}$alkylcarbonyl; or $C_{1-4}$alkyloxycarbonyl$C_{1-4}$alkylaminocarbonyl;

or $R^2$ is benzimidazole, or benzimidazole substituted with one or two substituents each independently selected from halo, trifluoromethyl, $C_{1-4}$alkyl, hydroxy, hydroxycarbonyl, or $C_{1-4}$alkyloxycarbonyl;

$R^3$ is a bivalent radical —$CH_2CH_2$— optionally substituted with halo or phenylmethyl;

or $R^3$ is a bivalent radical of formula

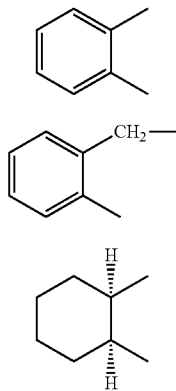

(b-1)

(b-2)

(b-3)

wherein said (b-1), (b-2), or (b-3) optionally can be substituted with one, two or three substituents each independently selected from halo, hydroxy, $C_{1-6}$alkyl, $C_{1-6}$alkyloxy, nitro, amino, cyano, trifluoromethyl, phenyl, or phenyl substituted with one or two substitutents each independently selected from halo, hydroxy, cyano, $C_{1-6}$alkyl, $C_{1-6}$alkyloxy, nitro, cyano, and trifluoromethyl;

aryl is phenyl, or phenyl substituted with amino, nitro or hydroxycarbonyl.

The term "amino acid residues" as used herein are the glycine, alanine, valine, leucine, isoleucine, methionine, proline, phenylalanine, tryptophan, serine, threonine, cysteine, tyrosine, asparagine, glutamine, aspartic acid, esters of aspartic acid, glutamic acid, esters of glutamic acid, lysine, arginine, and histidine amino acid radicals which are bound via their carbonyl group to the nitrogen atom of the rest of the molecule and which can be generally represented by "R—CH(NH$_2$)—CO—".

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; $C_{1-6}$alkyl is meant to include $C_{1-4}$alkyl and the higher homologues thereof having 5 or 6 carbon atoms, such as, for example, 2-methyl-butyl, pentyl, hexyl and the like; $C_{3-6}$cycloalkyl is generic to cyclopropyl, cyclobutyl, cyclopentyl and cyclohexyl; $C_{3-6}$alkenyl defines straight and branched chain unsaturated hydrocarbon radicals having from 3 to 6 carbon atoms, such as propenyl, butenyl, pentenyl or hexenyl; $C_{1-2}$alkanediyl defines methylene or 1,2-ethanediyl; $C_{1-5}$alkanediyl defines bivalent straight or branched chain hydrocarbon radicals containing from 1 to 5 carbon atoms such as, for example, methylene, 1,2-ethanediyl, 1,3-propanediyl, 1,4-butanediyl, 1,5-pentanediyl, and the branched isomers thereof; $C_{1-6}$alkanediyl includes $C_{1-5}$alkanediyl and the higher homologues thereof having 6 carbon atoms such as, for example, 1,6-hexanediyl and the like. The term "CO" refers to a carbonyl group.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R-or S-configuration; substituents on bivalent cyclic (partially) saturated radicals may have either the cis-or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable addition salts as mentioned hereinabove include pharmaceutically acceptable acid addition salts and are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Where the compounds of the invention carry an acidic moiety, suitable pharmaceutically acceptable base addition salts are possible which include alkali metal salts, e.g., sodium or potassium salts; alkaline earth metal salts, e.g., calcium or magnesium salts; and base addition salts formed with suitable organic ligands, e.g., primary, secondary, tertiary or quaternary ammonium salts, such as morpholinyl, tert-butylamino, and the like.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

Interesting compounds are those compounds of formula (I) wherein one or more of the following restrictions apply:
a) n is 0;
b) $R^3$ is a radical of formula (b-1) optionally substituted with halo or methoxy;
c) X represents —$CH_2$— or —$CH_2CH_2$—;
d) $R^2$ is a radical of formula (a-2) wherein $R^6$ is hydrogen;
e) $R^2$ is a radical of formula (a-2), (a-4), (a-6), or (a-7);
f) $R^2$ is benzimidazole optionally substituted with methyl, hydroxy, halo, trifluoromethyl, methyloxycarbonyl, or hydroxycarbonyl;
g) $R^1$ is $C_{1-6}$alkylcarbonyl, amino$C_{1-6}$alkylcarbonyl or an amino acid.

Particular compounds are those compounds of formula (I) wherein n is 0 and $R^3$ is a radical of formula (b-1) optionally substituted with halo or methoxy.

Preferred compounds are those compounds of formula (I) wherein n is 0, $R^3$ is a radical of formula (b-1) optionally substituted with halo or methoxy, and X represents —$CH_2$—.

Other preferred compounds are those compounds of formula (I) wherein n is 0, $R^3$ is a radical of formula (b-1) optionally substituted with halo or methoxy, and X represents —$CH_2CH_2$—.

Still other preferred compounds are those compounds of formula (I) wherein $R^1$ is $C_{1-6}$alkylcarbonyl, amino$C_{1-6}$alkylcarbonyl or an amino acid.

Compounds of formula (I-a), defined as compounds of formula (I) wherein $R^{1a}$ represents all $R^1$ substituents other than $C_{1-4}$alkyl substituted with amino, can be prepared by reacting an intermediate of formula (II) with an intermediate of formula (III) in the presence of 4-methyl-morpholine, in a reaction-inert solvent such as, e.g. dichloromethane of chloroform. Stirring may enhance the rate of the reaction. The reaction may conveniently be carried out at a temperature ranging between room temperature and the reflux temperature of the reaction mixture and, if desired, the reaction may be carried out in an autoclave at an increased pressure. Optionally said reaction is followed by an acid hydrolysis step to remove acid labile protecting groups, such as a tert-butyloxycarbonyl.

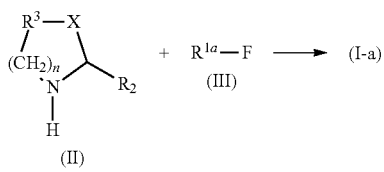

Alternatively, compounds of formula (I-a) can also be prepared by reacting an intermediate of formula (II) with an intermediate of formula (IV) in the presence of an appropriate activating agent, such as e.g. isobutyl chloroformate, in a reaction-inert solvent such as, e.g. dichloromethane, in the presence of a suitable base such as, e.g. triethylamine. Optionally said reaction is followed by an acid hydrolysis step to remove acid labile protecting groups, such as a tert-butyloxycarbonyl.

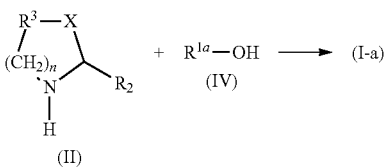

Compounds of formula (I-b), defined as compounds of formula (I) wherein $R^1$ represents $C_{1-6}$alkyl substituted with amino, can conveniently be prepared by submitting the corresponding starting compounds (I-b') wherein $R^1$ represents amino$C_{1-5}$alkylcarbonyl to an appropriate reduction reaction. Appropriate reduction reactions can be e.g. treatment with borane-tetrahydrofuran complex.

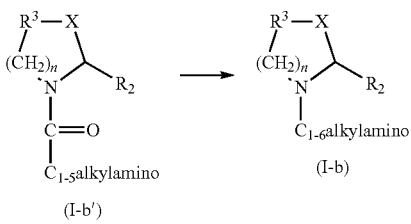

Compounds of formula (I-c), defined as compounds of formula (I) wherein $R^2$ represents a radical (a-2) wherein $R^6$ is hydrogen and $R^7$ is located at the 3-position of the imidazole moiety, can be prepared by reacting an intermediate of formula (V) with an intermediate of formula (VI) in the presents of potassium acetate in a suitable solvent such as methanol.

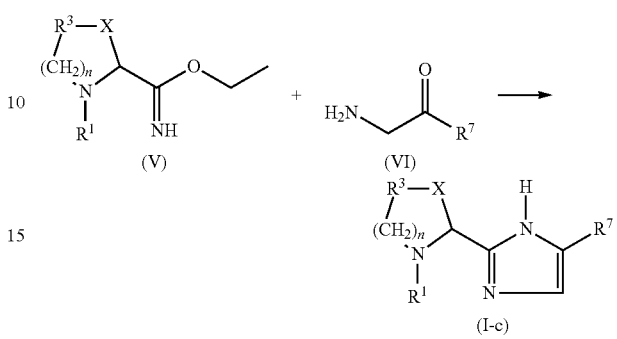

The compounds of formula (I) may further be prepared by converting compounds of formula (I) into each other according to art-known group transformation reactions.

The starting materials and some of the intermediates, such as e.g. intermediates of formula (III), (IV) and (VI), are known compounds and are commercially available or may be prepared according to conventional reaction procedures generally known in the art.

Compounds of formula (I) and some of the intermediates may have one or more stereogenic centers in their structure, present in a R or a S configuration, such as, e.g. the carbon atom bearing the $R^2$ substituent.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*].

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof are inhibitors of a membrane tripeptidyl peptidase responsible for the inactivation of endogenous neuropeptides such as cholecystokinis (CCKs) as evidenced in pharmacological example C-1.

In view of their TPP II inhibiting properties the compounds of the present invention are useful in treatment of conditions or disorders associated with TPP II activity such as, e.g. eating disorders, obesity, psychotic syndromes and associated psychiatric disorders.

In view of the utility of the compounds of formula (I), it follows that the present invention also provides a method of treating warm-blooded animals, including humans, (generally called herein patients) suffering from eating disorders, obesity, psychotic syndromes and associated psychiatric disorders Consequently a method of treatment is provided for inhibiting the activity of TPP II and/or relieving patients suffering from conditions, such as, for example, eating disorders, obesity, psychotic syndromes and associated psychiatric disorders.

Hence, the use of a compound of formula (I) as medicine is provided acting as an inhibitor of the CCK-inactivating peptidase tripeptidyl peptidase (TPP II) and/or for the treatment of eating disorders, especially obesity and/or for the treatment of psychotic syndromes and associated psychiatric disorders, which comprises a therapeutically effective amount of a compound of formula (I). Also provided is the use of a compound of formula (I) for the manufacture of a medicine for inhibiting the activity of TPP II and/or treating eating disorders, obesity, psychotic syndromes and associated psychiatric disorders. Both prophylactic and therapeutic treatment are envisaged.

It is believed that some of the compounds of the present invention, in particular compounds (153) to (181), may also have opioid activity such as delta-opioid ($\delta$), mu-opioid ($\mu$) and/or kappa-opioid ($\kappa$) activity. Opioid activity can be measured using the assays as described in pharmacological examples C.2 and C.3.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

EXPERIMENTAL PART

In the procedures described hereinafter the following abbreviations were used: "ACN" stands for acetonitrile; "THF", which stands for tetrahydrofuran; "DCM" stands for dichloromethane; and "MIK" stands for methyl isobutyl ketone.

For some chemicals the chemical formula was used, e.g. $CH_2Cl_2$ for dichloromethane, $CH_3OH$ for methanol, $NH_3$ for ammonia, HCl for hydrochloric acid, NaOH for sodium hydroxide, $NaHCO_3$ for sodium hydrogen carbonate, and $Na_2CO_3$ sodium carbonate.

In those cases the stereochemically isomeric form which was first isolated is designated as "A" and the second as "B", without further reference to the actual stereochemical configuration.

Preparative liquid chromatography was performed on a semi-preparative HPLC unit using a YMC ODS-A column (30×100 mm, 5 micron, temperature:ambient, flow rate: 35 mL/min, mobile phase: a) 10/90 acetonitrile/water with 0.1% trifluoroacetic acid, b) 90/10 acetonitrile/water with 0.1% trifluoroacetic acid, gradient:linear gradient from A to B over 9 minutes, UV detection at 254 nm.

A. Preparation of the Intermediates

Example A.1 a) 2,3-Dihydroxy-1H-indole-2-carboxamide (0.030 mol) was suspended in trichloromethane (400 ml). The mixture was cooled to 0° C. Triethylamine (0.045 mol) was added. Acetyl chloride (0.045 mol) was added over 2 minutes. After 30 minutes, TLC showed the reaction was incomplete. While the flask was still cool, more Triethylamine (6.26 ml) was added, followed 15 minutes later with more acetyl chloride (3.21 ml). TLC showed the reaction was still incomplete. The reaction was continued to allow to stir, cooled to 0° C., and more triethylamine (6.26 ml) was added. Over 2 minutes, more acetyl chloride (3.21 ml) was added neat. TLC showed 80% completion after 60 minutes, and no progress after 30 more minutes. A third portion of acetyl chloride and triethylamine was added. After an additional 15 minutes, ice cold water (200 ml) was added. The mixture was stirred for 10 minutes, filtered, and rinsed with water (3×100 ml) and trichloromethane (2×75 ml). The sample was allowed to dry overnight, yielding 4.71 g of (S)-1-acetyl-2,3-dihydro-1H-indole-2-carboxamide (intermediate 1, mp. >260° C.).

b) Intermediate (1) (0.02022 mol) was suspended in DCM (175 ml). The mixture was cooled to 0° C. Triethylamine (0.06066 mol) was added neat. Trichloroacetyl chloride (0.03033 mol) in DCM (20 ml) was added dropwise over 20 minutes. After 2 hours, ice water (200 ml) was added, the phases separated and the organic phase reextracted with 3 N HCl and then with a saturated aqueous $NaHCO_3$ solution. The organic phase was dried, filtered, and stripped to leave 4.61 g brown solid. The solid was triturated with ice cold diethylether (30 ml), filtered, and rinsed with ice cold diethylether (twice), yielding 3.12 g (83%) of (S)-1-acetyl-2,3-dihydro-1H-indole-2-carbonitrile (intermediate 2, mp. 134-135° C.).

c) Intermediate (2) (0.0151 mol) was suspended in diethylether (200 ml). Ethanol (0.0214 mol) was added, and the mixture was cooled to 0° C. HCl (gas) was bubbled in for 45 minutes. The mixture was removed from the ice bath and stirred. After 20 minutes, a residue collected on the wall sides. The walls were scratched, and a white solid precipitated out. After 1 hour the sample was filtered, rinsed with diethylether, air dried quickly, yielding 3.99 g of (S)-ethyl 1-acetyl-2,3-dihydro-1H-indole-2-carboximidate monohydrochloride (intermediate 3).

In analogy, ethyl 1-acetyl-2,3-dihydro-1H-indole-2-carboximidate monohydrochloride (intermediate 6) was prepared starting from 1-acetyl-2,3-dihydro-1H-indole-2-carbonitrile.

Example A.2 a) 5-chloro-2,3-dihydroxy-1H-indole-2-carboxylic acid, methyl ester (0.00761 mole) was dissolved in methanol (25 ml) and cooled to 0° C. $NH_3$ was bubbled in for 10 minutes. The flask was stoppered and allowed to warm to room temperature. The mixture was stirred overnight. TLC showed the reaction was mostly complete. The sample was concentrated to ±⅓ volume, cooled, and filtered, rinsing resulting solid with ice cold methanol (2 ml) and then dried ion the air, yielding 0.74 g of 5-chloro-2,3-dihydro-1H-indole-2-carboxamide (intermediate 7, mp. 151-152° C.).

b) Triethylamine (0.02080 mole) was added to intermediate (7) (0.09632 mole) dissolved in trichloromethane (700 ml). The mixture was cooled to 5° C. Acetyl chloride (0.2480 mole) was added over 2 minutes with stiffing. After 5 minutes, a precipitate formed. The ice bath was removed, and the container allowed to sit for 15 minutes. Ice water (250 ml) was added, and the mixture was stirred for 10 minutes. The sample was filtered, rinsed with water and trichloromethane. The solid was suspended in water (200 ml), and swirled for 10 minutes. Trichloromethane (200 ml) was added and the mixture was stirred, then filtered and rinsed with water and trichloromethane, and then dried to the air overnight, yielding 19.71 g of 1-acetyl-5-chloro-2,3-dihydro-1H-indole-2-carboxamide (intermediate 8).

c) Triethylamine (0.41291 mole) was added to intermediate (8) (0.08258 mole) suspended in dichloromethane (500 ml) at 0° C. Trichloroacetyl chloride (0.20645 mole) was added over 10 minutes. When the reaction appeared sluggish, an additional portion of triethylamine (20 ml) and then more trichloroacetyl chloride (7.6 ml) were added, and the mixture was stirred for 2 hours at low temperature. The ice bath was removed, and the mixture was allowed to sit for 2 hours. This resulted in a darker colored reaction, which was re-cooled to 0° C. Ice cold water (150 ml) was slowly added, and the mixture was stirred for 5 minutes. The layers were separated, and the organic phase was washed (ice cold 3N HCl, saturated NaHCO$_3$), dried, filtered, and concentrated. The residue was triturated in ice cold diethylether (40 ml). Filtration, rinsing with ice cold diethylether (10 ml), yielding 15.13 g of 1-acetyl-5-chloro-2,3-dihydro-1H-indole-2-carbonitrile (intermediate 9, mp. 140-142° C.).

d) HCl (as a 2 M solution) was added slowly to intermediate (9) until gas evolution was noted. Then stopped adding the prepared HCl (2N in diethylether), and suspended HCl in diethylether (150 ml) and then ethanol (0.042 mole) was added. The mixture was cooled to 0° C. and HCl (gas) was added over an hour, with an oil precipitating out. The reaction was diluted to 1 l with diethylether. More oil precipitates, and no solid formed after sitting for 1 hour. The diethylether was decanted off. The residue was diluted (diethylether, 500 ml). The solid begins to form, and the mixture was stirred for 2 hours. The sample was filtered, rinsing with diethylether. The sample was placed under vacuum, yielding 6.41 g of ethyl 1-acetyl-5-chloro-2,3-dihydro-1H-indole-2-carboximidate monohydrochloride (intermediate 10).

Example A.3 a) Bis (1,1-dimethylethyl)ester dicarbonic acid (0.07615 mol) in DCM (50 ml) was added over 5 minutes to 2,3-dihydro-1H-indole-2-methanol (0.07615 mol) in DCM (150 ml) at 0° C. The mixture was allowed to warm to room temperature and stirred overnight. The mixture was concentrated under reduced pressure and submitted to a Kogel Rohr distillation, yielding 11.98 g of 1,1-dimethylethyl 2,3-dihydro-2-(hydroxymethyl)-1H-indole-1-carboxylate (intermediate 11).

b) Dess-Martin Reagent (0.011 mol) was added neat over 1 minutes to intermediate (11) (0.010 mol) dissolved in DCM (35 ml). After 15 minutes, the ice bath was removed, and the mixture was allowed to warm to room temperature. More Dess-Martin Reagent (0.33 g) was added, and the mixture was stirred for 30 minutes more. The mixture was re-cooled to 0° C. and treated slowly with a partial suspension/solution of Na$_2$S$_2$O$_3$ (25 g) which had attempted to dissolve in a saturated aqueous NaHCO$_3$ (100 ml) solution. After 10 minutes, the mixture was removed from ice, and the layers were separated. More DCM was added, and the mixture was filtered. The organic was separated from the filtrate, and the combined organic phases were dried, filtered, concentrated and purified through flash column chromatography (eluent: 10% ethyl acetate:hexane, dissolving the sample in 3:1 ethyl acetate: hexane (5 ml)), yielding 1,1-dimethylethyl 2-formyl-2,3-dihydro-1H-indole-1-carboxylate (intermediate 12, mp. 85-87° C.).

Example A.4

A solution of 1-acetyl-2,3-dihydro-1H-indole-2-carbonitrile (0.00988 mol) and Triethylamine (0.0197 mole) in pyridine (50 ml) was treated with hydrogen sulfide (gas) at room temperature via a bubbler for 2 hours and the resultant saturated reaction mixture was closed and allowed to set for 16 hours. The reaction mixture was poured into 200 ml of an ice water slurry. A voluminous precipitate formed. The mixture was recooled in an ice bath and the precipitate was collected by suction filtration, washed with cold water, and air dried, yielding 1.62 g of 1-acetyl-2,3-dihydro-1H-indole-2-carbothioamide (intermediate 13, mp. 194-195° C.).

Example A.5

1-acetyl-2,3-dihydro-1H-indole-2-carbonitrile (0.0132 mole) was treated with water (54 ml) and the resulting suspension was treated sequentially with Na$_2$CO$_3$ (0.00726 mole) and NH$_2$OH.HCl 0.0145 mole). The mixture was treated with ethanol (26 ml) and heated to 80-90° C. Upon achieving reaction temperature, the mixture was still a suspension. Added another 26 ml of ethanol which afforded a clear solution. The reaction was heated for 2.5 hours and cooled to room temperature with stiffing. A voluminous precipitate formed which was collected by suction filtration, washed with cold distilled water, and air dried, yielding 2.23 g of 1-acetyl-2,3-dihydro-N-hydroxy-1H-indole-2-carboximidamide (intermediate 14, mp. 204-205° C.).

Example A.6

1-acetyl-2-(4-ethyl-1H-imidazol-2-yl)-2,3-dihydro-1H-indole (0.0035 mol) and HCl, 6N (50 ml) were combined under nitrogen atmosphere. The reaction mixture was heated immediately and the heating was continued for 3.5 hours. The mixture was allowed to cool to room temperature, then extracted with diethylether (2×75 ml), cooled to 0° C., alkalized (with cooled 3 N NaOH), then extracted with chloroform (3×60 ml). The combined organic layers were dried, filtered and the solvent was evaporated, yielding 0.79 g of 2-(4-ethyl-1H-imidazol-2-yl)-2,3-dihydro-1H-indole (intermediate 15).

Example A.7 a) To a suspension of 5-fluoro-1H-indole-2-carboxylic acid, ethyl ester (0.121 mole) in methanol (600 ml) was added Mg (0.36 mole). The mixture was in a 3-neck round bottom flask under argon at room temperature. The temperature of the reaction was monitored closely. After about 10 minutes, the mixture began to bubble, slowly at first and then more vigorously. The reaction temperature was maintained between 15 and 25° C. with intermittent applications of an ice bath. After 30 minutes, the bubbling had slowed. The mixture was allowed to stir at room temperature for three days. The mixture was partitioned between 600 ml of chloroform and 500 ml of saturated NH$_4$Cl solution. The organic layer was dried over MgSO$_4$ and concentrated to a brown oil. The oil was dissolved in ether and extracted with 3N HCl. The aqueous layer was washed with ether, basified with 3N NaOH, and extracted with chloroform. The extract was dried over MgSO$_4$ and concentrated, yielding 13.91 g of methyl 5-fluoro-2,3-dihydro-1H-indole-2-carboxylate (intermediate 16).

b) To 2M NH₃ in methanol (0.6 mol), cooled in an ice bath under Ar, was added intermediate (16) (0.0574 mol) dissolved in methanol (150 ml). The mixture was allowed to warm to room temperature and stir under argon for 6 hours. The reaction was concentrated to 150 ml and filtered. The solid was rinsed with a small amount of cold methanol and allowed to dry, yielding 2.33 g of 5-fluoro-2,3-dihydro-1H-indole-2-carboxamide (intermediate 17, mp. 197-199° C.).

c) To a mixture of intermediate (17) (0.0094 mole) in DCM (30 ml), cooled in an ice bath under argon, was added triethylamine (0.031 mole) followed by acetyl chloride (0.031 mole). The resulting mixture was allowed to return to room temperature. After stifling for 6 hours, the mixture was cooled in an ice bath and 50 ml of water was added. The mixture was allowed to stir about 20 minutes, was filtered and the solid was allowed to dry to obtain 1.58 g of 1-acetyl-5-fluoro-2,3-dihydro-1H-indole-2-carboxamide (intermediate 18, mp. 232-235° C.).

d) To a suspension of intermediate (18) (0.0076 mole) in DCM (30 ml), cooled in an ice bath under argon, was added triethylamine (0.0228 mole) followed by trichloroacetyl chloride (0.0115 mole). The mixture was allowed to warm to room temperature and stir for 2 hours. The mixture was washed with water, 2N HCl, and saturated NaHCO₃. The organic layer was dried and concentrated. The concentrate was triturated in ether and purified on silica gel column, eluting with 50% ethyl acetate in hexane. The desired fractions were combined and concentrated. The residue was triturated in ether and the solid collected by filtration and allowed to dry, yielding 0.30 g of 1-acetyl-5-fluoro-2,3-dihydro-1H-indole-2-carbonitrile (intermediate 19, mp. 93-95° C.).

e) A solution of intermediate (19) (0.004 mole) and HCl/diethylether (60 mL) was cooled in an ice bath under argon. Ethanol (0.0075 mole) was added. HCl was bubbled into the solution for 50 minutes until the mixture became homogeneous. The mixture was allowed to slowly warm to room temperature and stir for 4 hours. The ether was decanted off and dissolved in methanol. The methanol solution was concentrated in vacuum and the residue was used as is for the next step, yielding ethyl 1-acetyl-5-fluoro-2,3-dihydro-1H-indole-2-carboximidate monohydrochloride (intermediate 20).

Example A.8 a) 2,3-dihydro-5-methoxy-1H-indole-2-carboxylic acid methyl ester (0.084 mole) and 2M NH₃ in methanol (500 ml) were combined and stirred at room temperature under argon over the weekend. The solution was concentrated to 100 ml, cooled in an ice bath, and filtered. The solid was rinsed with a small amount of cold methanol and dried. The residue was triturated in methanol/ACN and filtered, yielding 4.56 g of 2,3-dihydro-5-methoxy-1H-indole-2-carboxamide (intermediate 21, mp. 228-229° C.).

b) Triethylamine (0.0106 mole) then acetyl chloride (0.0106 mole) were added to a solution of intermediate (21) (0.0032 mole) in DCM (40 ml) cooled in an ice bath under argon. The mixture was allowed to slowly warm to room temperature and stir overnight. The mixture was cooled in an ice bath and ice cold water (30 ml) was added. After stirring for 10 minutes, the mixture was filtered, and the solid was allowed to dry overnight. The residue was suspended in 50 ml water. The suspension was allowed to stir for 30 minutes, filtered, and dried overnight, yielding 0.40 g of 1-acetyl-2,3-dihydro-5-methoxy-1H-indole-2-carboxamide (intermediate 22, mp. 196-197° C.).

c) To a suspension of intermediate (22) (0.022 mole) in DCM (150 ml), cooled in an ice bath under argon, was added triethylamine (0.066 mole) then trichloroacetyl chloride (0.033 mole). The mixture was allowed to slowly warmed to room temperature overnight. The mixture was washed with water, 2N HCl, and saturated NaHCO₃. The organic phase was dried, concentrated and triturated in ether and the solid collected, yielding 1-acetyl-2,3-dihydro-5-methoxy-1H-indole-2-carbonitrile (intermediate 23, mp. 108-110° C.).

d) To a solution of intermediate (23) (0.0154 mole) and ethanol (0.0231 mole) in 1M HCl/diethylether (200 ml), cooled in an ice bath was bubbled HCl (gas) for 60 minutes. The ice bath was maintained for 45 minutes, and the mixture was concentrated at room temperature under vacuum to 200 ml of an oily precipitate. The residue was triturated to a brown solid that became an oil after decanting off the diethylether. The residue was washed with diethylether twice, dissolved in methanol, and used without further purification for further synthesis, yielding ethyl 1-acetyl-2,3-dihydro-5-methoxy-1H-indole-2-carboximidate monohydrochloride (intermediate 24).

Example A.9

(S)-2-(Tert-butoxycarbonylamino)butyric acid (0.010 mol) dissolved in DCM (25 ml) was placed in a cooling bath at −10° C. Pyridine (0.010 mol) was added, followed by 2,4,6-trifluoro-1,3,5-triazine (0.0345 mol). The mixture was stirred under nitrogen. After one hour, ice cold water (75 ml) was added. More DCM (45 ml) was added, and the mixture was shaken. The organic phase was separated, washed with ice cold water again (100 ml), then the organic phase dried, filtered, and concentrated to yield 2.29 g of (S)-1,1-dimethylethyl [1-(fluorocarbonyl)propyl]-carbamate (intermediate 25).

Example A.10

Compound (8) (0.00170 mol) was dissolved in HCl, 6N (20 ml), and immediately warmed in an oil bath at 100° C. under nitrogen for 200 minutes. The heat was turned off, and the sample was cooled to 0° C. 3 N NaOH (35 ml) was slowly added. Basification was completed with saturated NaHCO₃. The sample was extracted with chloroform. The combined organic phases were dried, filtered, and the resulting solution was used without further purification in further synthesis, yielding (S)-2,3-dihydro-2-(4-propyl-1H-imidazol-2-yl)-1H-indole (intermediate 5).

Example A.11

A mixture of intermediate (13) (0.00844 mol) in ethanol (180 ml) was treated with 1-bromo-2-butanone (0.0085 mol) in one portion and heated to reflux for 16 hours. The reaction mixture was cooled to room temperature and extracted between ether and cold 1 M NaOH (aqueous). The organic fraction was dried over MgSO₄ and concentrated in vacuo to afford a dark solid which was subjected to silica gel flash column chromatography (eluent 100% DCM to 97:3 DCM/ diethyl ether), yielding 0.91 g of 2-(4-ethyl-2-thiazolyl)-2,3-dihydro-1H-indole (intermediate 4).

Example A.12

3-(2-oxo-2-phenyl-ethylcarbamoyl)-3,4-dihydro-1H-isoquinoline-2-carboxylic acid tert butyl ester

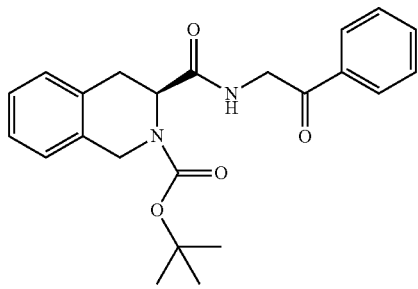

3,4-Dihydro-1H-isoquinoline-2,3-dicarboxylic acid-2-tertbutyl ester (2.77 g, 10 mmol) and 2-amino-1phenyl-ethanone (1.71 g, 10 mmol), and HOBT (1-hydroxybenzo-triazole) (2.70 g, 20 mmol) were dissolved in dichloromethane (100 ml). The solution was cooled to 0° C. and then (4-dimethylamino-butyl)-ethyl-carbodiimide (2.29 g, 12 mmol) was added followed by NMM (N-methyl-morpholine) (1.31 g, 13 mmol).

The reaction mixture was then warmed to room temperature. After 72 hours the reaction mixture was extracted with water, and the organic phase extracted consecutively with saturated NaHCO₃, 2N citric acid and NaHCO₃, dried over MgSO₄, filtered and concentrated to yield the title product as a yellow foam. Liquid chromatography (LC) indicated the compound was 86% pure (214 nm), and was used without further purification.

Example A.12a

Dehydration of 3-(2-oxo-2-phenyl-ethylcarbamoyl)-3,4-dihydro-1H-isoquinoline-2-carboxylic acid benzyl ester (prepared in a similar manner as 3-(2-oxo-2-phenyl-ethylcarbamoyl)-3,4-dihydro-1H-isoquinoline-2-carboxylic acid tert butyl ester of Example A.12) with POCl₃ yields the following intermediate compound:

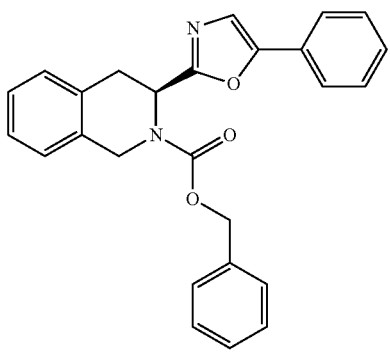

The CBZ group is readily removed from the resulting oxazole by treatment with iodotrimethylsilane. The resulting nor-amine oxazole intermediate can be carried on to compound 170 following similar procedures as described for its analogous imidazole intermediates.

Example A.13

3-(4-phenyl-1H-imidazol-2-yl)-3,4,-dihydro-1H-isoquinoline-2-carboxylic acid tert-butyl ester

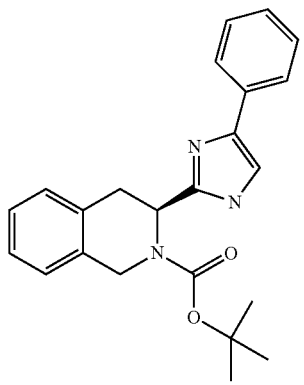

The product prepared in Example A.12 above (3.55 g, 9 mmol), NH₄OAc (ammonium acetate) (20.8 g, 270 mmol) and AcOH (acetic acid) (30 mL) were combined at room temperature and the reaction mixture was warmed on a steam bath for about 3 hours. The reaction mixture was then cooled to room temperature and poured into an ice slurry mix (400 g). To this mixture was added concentrated ammonium hydroxide (50 mL) and ethyl ether. The layers were separated, and the aqueous phase washed with a second portion of ethyl ether. The organic phases were combined, dried over MgSO₄, filtered, and concentrated under reduced pressure to yield a brown foam. This sample was purified by preparative HPLC to yield the purified title compound as a white powder. LC indicated the sample was 96% pure at 214 nm.

Measured MW (MH⁺): 376

Example A.14

3-(4-phenyl-1H-imidazol-2-yl)-1,2,3,4-tetrahydro-isoquinoline

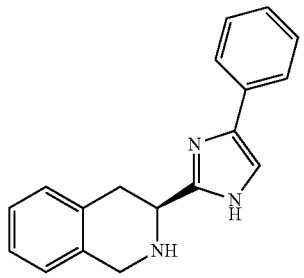

Trifluoroacetic acid (TFA) (4 mL) was cooled in a test tube to about 0° C. To the cool solvent was then added the product prepared in Example A.13 (0.75 g, 2 mmol) above. The reaction mixture was allowed to warm to room temperature over about 45 minutes. Excess TFA was removed under a stream of $N_2$ gas. The residue was partitioned between dichloromethane (15 mL) and saturated $NaHCO_3$. The aqueous phase was then re-extracted with a second portion of dichloromethane and the organic phases combined, dried over $MgSO_4$ and filtered, to yield the title compound in dichloromethane solution. The filtrate was used in the next step (Example A.15) without further purification or isolation.

Measured MW (MH+): 276

Example A.15

[1-(4-tert-butoxy-benzyl)-2-oxo-2-[3-(4-phenyl-1H-imidazol-2-yl)-3,4-dihydro-1H-isoquinolin-2-yl]-ethyl]-carbamic acid tert-butyl ester

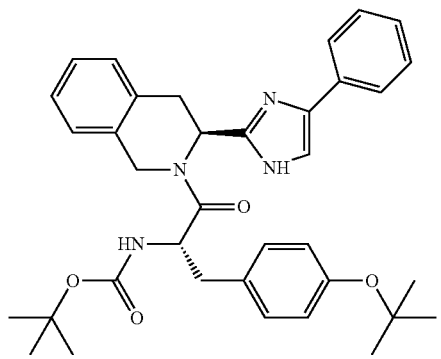

2-Tert-butoxycarbonylamino-3-(4-tert-butoxy-phenyl)-propionic acid (0.74 g, 2.2 mmol) was dissolved in dichloromethane (40 mL) and the reaction mixture cooled to about 0° C. To the solution was then added NMM (0.21 g, 2.1 mmol) followed by isobutyl chloroformate (0.27 g, 2 mmol, 0.26 mL) and the solution was allowed to stand for about 1.25 hours. To the reaction mixture was then added the product prepared in Example A.14 (0.55 g, 2 mmol) and the reaction mixture stiffed for about 16 hours. The reaction mixture was then extracted with water, saturated $NaHCO_3$, 2N citric acid, saturated $NaHCO_3$, dried over $MgSO_4$, filtered and concentrated to yield the title product as a foam. Measured MW (MH+): 595.

A bromine can be introduced at the 5-position of the imidazole moiety of this intermediate compound by reacting said intermediate compound with 1 equivalent of $Br_2$ at 0° C. in chloroform.

A chlorine can be introduced at the 5-position of the imidazole moiety of this intermediate compound by reacting said intermediate compound with N-chloro-succinimide.

Example A.16

3-(5-methyl-4-phenyl-1H-imidazol-2-yl)-3,4-dihydro-1H-isoquinoline-2-carboxylic acid tert-butyl ester

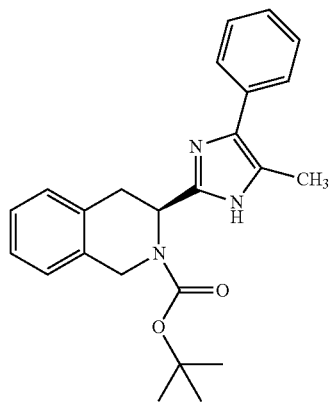

3-Formyl-3,4-dihydro-1H-isoquinoline-2-carboxylic acid tert-butyl ester (1.83 g, 7 mmol) was combined with AcOH (25 mL) to which was immediately added 1-phenyl-propane-1,2-dione (3.11 g, 21 mmol) and $NH_4OAc$ (13.49 g, 175 mmol). The reaction mixture was then placed on a steam bath and heated under an argon atmosphere for 20 minutes. The reaction mixture was cooled in an ice bath and then added to an ice slurry (44 g). The resulting mixture was basified by addition of concentrated $NH_4OH$ (50 mL) and then extracted twice with diethyl ether (150 mL each). The combined organic phases were dried over $MgSO_4$, filtered and concentrated to yield crude product. This material was purified by preparative HPLC to yield the title compound as a white solid.

Measured MW (MH+): 390

Example A.17

3-(5-methyl-4-phenyl-1H-imidazol-2-yl)-3,4,-dihydro-1H-isoquinoline

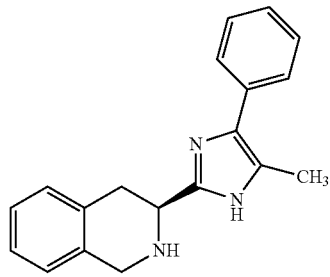

To a solution of TFA (5 mL) cooled to about 0° C. was added the compound prepared in Example A.16 (1.10 g, 2.82 mmol) and the reaction mixture stirred for about 30 minutes. The reaction mixture was then removed from the ice bath and allowed to warm to room temperature. Excess TFA was removed under a stream of N$_2$. The residue was partitioned between saturated NaHCO$_3$ and dichloromethane. The aqueous phase was washed with a second portion of dichloromethane and the organic phases combined. The combined organic phase was dried over Na$_2$SO$_4$, then filtered to yield the title product as a solution in dichloromethane, which was used without further purification or isolation.

Example A.18

[1-(4-tert-butoxy-benzyl)-2-[3-(5-methyl-4-phenyl-1H-imidazol-2-yl)-3,4-dihydro-1H-isoquinolin-2-yl]-2-oxo-ethyl]-carbamic acid tert-butyl ester

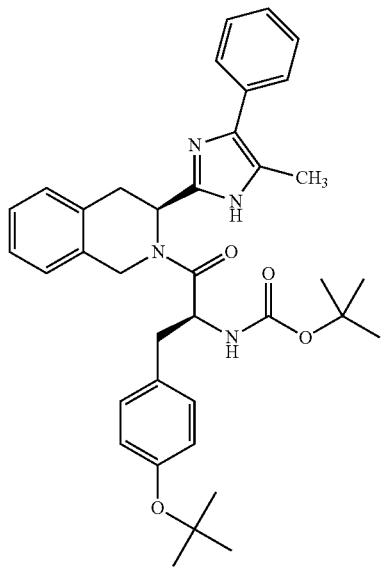

2-Tert-butoxycarbonylamino-3-(4-tert-butoxy-phenyl)-propionic acid (0.74 g, 2.2 mmol) was dissolved in dichloromethane (60 mL), cooled to about 0° C. To the reaction mixture was then added NMM (0.30 g, 2.97 mmol), followed by isobutyl chloroformate (0.39 g, 2.82 mmol, 0.37 mL). The solution was allowed to stand at 0° C. for about 90 minutes. To the reaction mixture was then added the product prepared in Example A.17 (2.82 mmol) as a solution in dichloromethane. The reaction mixture was then warmed to room temperature. After 16 h the reaction mixture was extracted sequentially with water, saturated NaHCO$_3$, 2N citric acid, saturated NaHCO$_3$, then dried over MgSO$_4$, filtered and concentrated to yield crude product. This material was purified via preparative HPLC to yield the title product as a whitish foam.

Measured MW (MH$^+$): 609

B. Preparation of the Final Compounds

Example B.1

4-Methylmorpholine (0.003 mol) was added to intermediate (5) (0.003 mol) dissolved in chloroform (80 ml). After cooling to 0° C., intermediate (25) (0.003 mol) was added neat as an oil. After 27 minutes, the reaction mixture was washed with water, saturated NaHCO$_3$, and brine, dried, filtered, and concentrated, yielding [2S-[1(R*),2R*]]-1,1-dimethylethyl [1-[[2,3-dihydro-2-(4-propyl-1H-imidazol-2-yl)-1H-indol-1-yl]-carbonyl]propyl]-carbamate (compound 14).

Example B.2

To intermediate (3) (0.047 mole) in methanol (200 ml) was added potassium acetate (0.199 mole). The mixture was heated to reflux under argon. To this was slowly added a solution of 1-amino-2-pentanone hydrochloride (0.094 mole) in methanol (95 ml) over 45 minutes. After the addition was complete, the mixture was allowed to stir overnight at reflux, then concentrated. The concentrate was taken up in DCM and washed with saturated NaHCO$_3$. The aqueous layer was extracted with DCM. The combined organic extracts were dried and concentrated to a solid residue. The residue was purified by trituration with diethyl ether and ACN and optionally further purified by column chromatography, yielding 5.83 g of (S)-1-acetyl-2,3-dihydro-2-(4-propyl-1H-imidazol-2-yl)-1H-indole (compound 8, mp. 174-175° C.).

Example B.3

Intermediate (12) (0.00101 mole), 2-3-hexanedione (0.004 mole), and ammonium acetate (0.025 mole) were combined in acetic acid (4 ml), and immediately placed on a steam bath for 15 minutes. After 2 hours at room temperature, the reaction was poured into ice water (100 ml), basified with 3N NaOH, and extracted with diethylether (twice). The organic phases were combined, dried, filtered, and concentrated. The residue was taken up in diethylether, concentrated and then purified by prep LC, yielding 0.440 g of 1,1-dimethylethyl 2,3-dihydro-2-(5-methyl-4-propyl-1H-imidazol-2-yl)-1H-indole-1-carboxylate (compound 99).

Analogously, compound (80) was prepared by reacting intermediate (12) with the respective aldehyde of 1,1,1-trifluoro-3,3-dibromoacetone.

Example B.4

N-[(1,1-dimethylethoxy)carbonyl]-N-methyl-L-alanine (0.00181 mol) was dissolved in DCM and cooled to 0° C. Triethylamine (0.00181 mol), then isobutyl chloroformate (0.00181 mol) were added, and the mixture was stirred at 0° C. for 70 minutes. Intermediate (5) (0.00181 mol) in DCM (6 ml) was added. The mixture was allowed to warm to room temperature and stirred overnight. The mixture was extracted (water, saturated NaHCO$_3$), dried, filtered, and concentrated. The residue was purified by HPLC. The pure fractions were collected and the solvent was evaporated, yielding 0.380 g of [2S-[1(R*),2R*]]-1,1-dimethylethyl [2-[2,3-dihydro-2-(4-propyl-1H-imidazol-2-yl)-1H-indol-1-yl]-1-methyl-2-oxo-ethyl]methyl-carbamate (compound 63, mp. 77-80° C.).

Example B.5

Compound 14 (0.0073 mole) and trifluoroacetic acid (5 ml), both precooled in an ice bath, were combined and allowed to slowly return to room temperature under nitrogen. After 1 hour, the mixture was concentrated. The concentrate was dissolved in water and extracted with diethylether. The aqueous layer was basified with saturated NaHCO$_3$ and extracted twice with chloroform. The combined organic extracts were dried over MgSO$_4$ and concentrated. The residue was dissolved in ether and treated with 3 ml of 1M HCl in ether. The precipitate was filtered and dried under vacuum. The residue was partitioned between saturated NaHCO$_3$ and chloroform. The organic layer was dried over MgSO$_4$ and concentrated. The concentrate was purified on a Biotage column, eluting with 5% MeOH in chloroform. The residue was dissolved in ether and treated with ±2 ml of 1M HCl in diethyl ether. The solid was collected by filtration under nitrogen and dried under vacuum overnight, yielding 0.364 g of [2S-[1(R*),2R*]]-α-ethyl-2,3-dihydro-β-oxo-2-(4-propyl-1H-imidazol-2-yl)-1H-indole-1-ethanamine dihydrochloride dihydrate (compound 15, mp. 132-140° C.).

Example B.6

A suspension of intermediate (13) (0.0102 mole) in n-butanol (200 ml) was treated with butanoic acid hydrazide (0.0254 mole), stirred for 10 minutes, and then heated to reflux for 10 days. The reaction was cooled, concentrated in vacuo, distributed between DCM and distilled water. The concentrated organic phase was subjected to reverse phase preparatory column chromatography to give 1-acetyl-2,3-dihydro-2-(5-propyl-1H-1,2,4-triazol-3-yl)-1H-indole (compound 91).

Example B.7 a) A solution of the compound 91 (0.42 g) in ethanol (25 ml) was treated with an aqueous NaOH solution (3 M, 25 mL) and the reaction mix was refluxed for 24 hours. The reaction was cooled, diluted with ethyl acetate, and treated with cold distilled water. The layers were separated and the aqueous fraction was extracted 5 times with ethyl acetate and the combined organic fractions were dried, concentrated and purified by preparatory column chromatography yielding 2,3-dihydro-2-(5-propyl-1H-1,2,4-triazol-3-yl)-1H-indole.

b) A solution of 2,3-dihydro-2-(5-propyl-1H-1,2,4-triazol-3-yl)-1H-indole (0.00017 mole) in DCM (5 ml) was treated with N-ethyl-N-(1-methylethyl)-2-propanamine (0.00072 mole) then (2-fluoro-2-oxoethyl)-9H-fluoren-9-yl-carbamic acid methyl ester (0.00070 mole). The reaction was stirred at room temperature for 15 hours. The reaction was diluted with DCM, treated twice with saturated NaHCO$_3$, and dried over Na$_2$SO$_4$ and concentrated. The residue was subjected to reverse phase prep column chromatography to obtain 0.02 g of the desired mono-adduct and 0.02 g of a bis-adduct that was completely converted to the desired mono-adduct by treatment with the prep chromatography eluent (0.1% trifluoroacetic acid in water/acetonitrile). These were combined, yielding 0.03 g of H-fluoren-9-ylmethyl [2-[2,3-dihydro-2-(5-propyl-1H-1,2,4-triazol-3-yl)-1H-indol-1-yl]-2-oxoethyl]-carbamate.

c) A solution of H-fluoren-9-ylmethyl [2-[2,3-dihydro-2-(5-propyl-1H-1,2,4-triazol-3-yl)-1H-indol-1-yl]-2-oxoethyl]-carbamate (0.00006 mole) in DCM (10 ml) was treated with piperidine (0.010 mole) and stirred at room temperature for 1 hour. The completed reaction was concentrated in vacuo and subjected to reverse phase prep column chromatography, yielding 0.02 g of 2,3-dihydro-β-oxo-2-(5-propyl-1H-1,2,4-triazol-3-yl)-1H-indole-1-ethanamine trifluoroacetate (1:1) (compound 92).

Example B.8

A mixture of intermediate (14) (0.00898 mole) and butanoyl chloride (0.0094 mole) in pyridine (140 ml) was stirred at room temperature for 40 hours and then heated to reflux. After 21 hours the reaction was cooled and concentrated in vacuo. The residue was extracted between DCM and saturated aqueous NaHCO$_3$ and the organic fraction was dried over Na$_2$SO$_4$, filtered, and concentrated. The residue was subjected to silica gel flash column chromatography (eluent 100% CH$_2$Cl$_2$ to 95/5 CH$_2$Cl$_2$/ether), yielding 1-acetyl-2,3-dihydro-2-(5-propyl-1,2,4-oxadiazol-3-yl)-1H-indole (compound 89, mp. 93-94° C.).

Example B.9 a) A solution of compound 89 (0.0035 mole) in ethanol (60 ml) was treated with 3M NaOH (60 ml), and the reaction mix was heated to 55-60° C. for 5.5 hours. The reaction was rapidly cooled in an ice bath, diluted with DCM, and treated with cold distilled water. The layers were separated and the aqueous fraction was extracted three times with DCM. The organic fractions were combined, washed once with 1M NaOH, and dried over Na$_2$SO$_4$ and concentrated in vacuo. The residue was purified by prep column chromatography, yielding 0.45 g of 2,3-dihydro-2-(5-propyl-1,2,4-oxadiazol-3-yl)-1H-indole.

b) A solution of 2,3-dihydro-2-(5-propyl-1,2,4-oxadiazol-3-yl)-1H-indole (0.0011 mole) in DCM (10 ml) was treated with N-methyl-N-(1-methylethyl)-2-propanamine (0.40 mL) then (2-fluoro-2-oxoethyl)-9H-fluoren-9-yl carbamic acid methyl ester (0.67 g). The reaction was stirred at room temperature for 40 hours and treated with another portion each of N-methyl-N-(1-methylethyl)-2-propanamine then (2-fluoro-2-oxoethyl)-9H-fluoren-9-yl carbamic acid methyl ester and stirred at room temperature for two days. The reaction was diluted with DCM, treated twice with saturated NaHCO$_3$, and dried over Na$_2$SO$_4$, and concentrated. The residue was subjected to reverse phase prep column chromatography, yielding 0.35 g of 9H-fluoren-9-ylmethyl [2-[2,3-dihydro-2-(5-propyl-1,2,4-oxadiazol-3-yl)-1H-indol-1-yl]-2-oxoethyl]-carbamate.

c) 9H-fluoren-9-ylmethyl [2-[2,3-dihydro-2-(5-propyl-1,2,4-oxadiazol-3-yl)-1H-indol-1-yl]-2-oxoethyl]-carbamate (0.35 g) was dissolved in DCM (40 ml), treated with piperidine (0.50 ml), and stirred at room temperature for 18 hours. The completed reaction was concentrated in vacuo and subjected to reverse phase prep column chromatograph, yielding 0.13 g of 2,3-dihydro-β-oxo-2-(5-propyl-1,2,4-oxadiazol-3-yl)-1H-indole-1-ethanamine trifluoroacetate (1:1) (compound 90, mp. 160-162° C.).

Example B.10

2,3-dihydro-2-(4-propyl-1H-imidazol-2-yl)-1H-indole (0.0024 mol) and 1,3-isobenzofurandione (0.0026 mol) were heated to 100° C. in a 25 ml pear shaped flask under argon for 2 hours. The mixture was dissolved in methanol and heated to reflux for 15 hours. The reaction mixture was concentrated and taken up in DCM, washed with water and 3 N NaOH. The basic aqueous extract was acidified with 6 N HCl and extracted with DCM. This organic extract was dried over MgSO$_4$ and concentrated. The concentrate was triturated in ether and collected. This was further purified, together with the acidic aqueous solution, by prep liquid chromatography, yielding 0.23 g of 2-[[2-(4-ethyl-1H-imidazol-2-yl)-2,3-dihydro-1H-indol-1-yl]carbonyl]-benzoic acid trifluoroacetate (1:1) (compound 85, mp. 98-103° C.).

Example B.11

1-Isocyanato-2-nitro-benzene (0.002 mol) was added to a solution of intermediate (15) (0.016 mol) in THF (10 ml). The mixture was stirred at room temperature under argon for 5 hours. The mixture was diluted with hexanes, filtered, and allowed to dry, yielding 0.34 g of 2-(4-ethyl-1H-imidazol-2- yl)-2,3-dihydro-N-(2-nitrophenyl)-1H-indole-1-carboxamide (compound 77, mp. 208-209° C.).

Example B.12

To a mixture of compound 77 (0.0006 mol), Raney Nickel (0.02 g; 50% slurry in water), and methanol (20 ml) was added hydrazin. Water (0.003 mol). The resulting mixture was heated to reflux for 2 hours. After cooling to room temperature, the mixture was carefully filtered through celite and the filtrate was concentrated. The residue was triturated in ether and filtered. The residue was purified by prep liquid chromatography, yielding 0.24 g of N-(2-aminophenyl)-2-(4-ethyl-1H-imidazol-2-yl)-2,3-dihydro-1H-indole-1-carboxamide trifluoroacetate (1:2) (compound 79, mp. 106-108° C.).

Example B.13

A mixture of compound 16 (0.00697 mole) in THF (70 ml) was treated with of sodium hydride (0.007 mole) in one portion and stirred at ambient temperature for 16 hours. Iodomethane (0.0071 mole) was introduced in one portion. After stirring at ambient temperature for 24 hours, more sodium hydride (0.007 mole) was added in one portion under an argon atmosphere. The flask was restoppered after effervescence had subsided, and stirred for 16 hours. The completed reaction was cooled in an ice bath, poured into DCM, and treated with cold water. The layers were separated and the aqueous was extracted three times with DCM. The combined organic fractions were washed with sat $NaHCO_3$, dried over $Na_2SO_4$, and concentrated. The residue was subjected to flash silica gel column chromatography (DCM to ether to 9:1 ether/THF). The appropriate fractions were combined. The residue was taken up in ether and placed in the freezer. Crystallization occurred, yielding 0.55 g (29.3%) of 1-acetyl-2-(4-ethyl-1-methyl-1H-imidazol-2-yl)-2,3-dihydro-1H-indole (compound 132, mp. 105-106° C.). The second set of fractions were combined. The residue was taken up in ether and placed in the freezer. Observed crystallization occurred, yielding 0.38 g of 1-acetyl-2-(4-ethyl-1-methyl-1H-imidazol-2-yl)-2,3-dihydro-1H-indole (compound 133, mp. 135-137° C.).

Example B.14

Compound 80 (0.001 mole) was suspended in 1N NaOH (12 ml). The mixture was vigorously stiffed and heated to 88° C. under nitrogen for 1 hour. After stiffing at room temperature for 3 hours, the mixture was cooled to 0° C., slowly neutralized with 1M HCl to precipitate some solid. The solid was filtered, rinsing with ice cold water. The aqueous phase was extracted twice, dried, filtered, concentrated and dried, yielding 0.140 g of 1,1-dimethylethyl 2-(4-carboxy-1H-imidazol-2-yl)-2,3-dihydro-1H-indole-1-carboxylate (compound 117).

Example B.15

1-Hydroxybenzotriazole hydrate (0.00036 mole), glycine methylester, hydrochloride (0.00047 mole), 4-methylmorpholine (0.00055 mole), and N'-(ethylcarbonimidoyl)-N,N-dimethyl-1,3-propanediamine monohydrochloride (0.00047 mole) were added to compound 117 (0.00036 mole) dissolved in DCM (30 ml) at 0° C. The mixture was allowed to warm to room temperature under nitrogen, and stirred overnight. The mixture was extracted with water, saturated $NaHCO_3$, 2N citric acid, then saturated $NaHCO_3$, dried, filtered, and concentrated, yielding 0.100 g (69%) of 1,1-dimethylethyl 2,3-dihydro-2-[4-[[(2-methoxy-2-oxoethyl)amino]carbonyl]-1H-imidazol-2-yl]-1H-indole-1-carboxylate (compound 118).

Example B.16

Compound 61 (0.00028 mol) was treated with 3N NaOH (3 ml) and allowed to stir for 20 minutes at room temperature. The solution was then treated with 3 ml of 3 N HCl and extracted with chloroform. The material stayed in the aqueous layer. The aqueous layer was purified by preparative liquid chromatography, yielding 0.12 g of 2-[1-(aminoacetyl)-2,3-dihydro-1H-indol-2-yl]-1H-benzimidazole-5-carboxylic acid monohydrate trifluoroacetate (1:2) (compound 62, mp. 208-211° C.).

Example B.17

Compound 102 (0.00238 mole) was dissolved in 40 ml of methanol and combined with 1N KOH (50 mL). The reaction was warmed to 40° C. under argon overnight. The heat was increased to 55-60° C. for an additional overnight heating. The reaction was then cooled to room temperature, filtered, and at 0° C. slowly neutralized with 1N HCl. The sample was extracted 5 times with DCM, combined, and dried over $Na_2SO_4$. This organic solution was filtered and used in further synthesis without further purification, yielding 1,1-dimethylethyl 2-(4-carboxy-5-propyl-1H-imidazol-2-yl)-2,3-dihydro-1H-indole-1-carboxylate (compound 105).

Example B.18

1-Hydroxybenzotriazole hydrate (0.00318 mole) was added to a solution of compound 105 (0.00159 mole) in DCM (160 mL) at room temperature. N,N'-methane-tetrayl-biscyclohexanamine (0.00206 mole) was added neat at room temperature. After 60 minutes, $NH_3$ gas was bubbled in for 5 minutes, and a solid precipitated out. The mixture was allowed to sit over the weekend. The mixture was filtered, and the filtrate was extracted with saturated $NaHCO_3$. The organic phases were dried over $MgSO_4$, filtered, and concentrated. The residue was purified by liquid chromatography, yielding 0.21 g of 1,1-dimethylethyl 2-[4-(aminocarbonyl)-5-propyl-1H-imidazol-2-yl]-2,3-dihydro-1H-indole-1-carboxylate (compound 106).

Example B.19

1-Hydroxybenzotriazole hydrate (0.00158 mole) was added to a solution of compound 105 (0.00079 mole) in DCM (80 ml). Glycine methylester hydrochloride (0.00103 mole), N'-(ethylcarbonimidoyl)-N,N-dimethyl-1,3 propanediamine monohydrochloride (0.00103 mole) and 4-methylmorpholine (0.00103 mole) were added. THF (25 mm) was added. The reaction was stirred at room temperature for 3 days. The mixture was extracted with water. The organic phase was washed with saturated $NaHCO_3$, 2N citric acid, saturated $NaHCO_3$, dried over $MgSO_4$, filtered, and concentrated, yielding 0.20 g of 1,1-dimethylethyl 2,3-dihydro-2-[4-[[(2-methoxy-2-oxoethyl)amino]carbonyl]-5-propyl-1H-imidazol-2-yl]-1H-indole-1-carboxylate (compound 109).

Example B.20

Compound 81 (0.0005 mole) was suspended in 1N NaOH (6 ml) under argon. The mixture was immediately heated to 80° C. for 60 minutes. At room temperature, chloroform (6 ml) then (2-fluoro-2-oxoethyl)-1,1-dimethylethyl carbamic acid ester (0.001 mole) were added. The mixture was stirred overnight. The layers were separated. The aqueous phase was cooled, acidified, and extracted twice with chloroform. The latter organic phases were combined, dried, filtered, and concentrated. The sample was purified by prep HPLC, yielding 0.040 g of 2-[1-[[[(1,1-dimethyletoxy)carbonyl]-amino]acetyl]-2,3-dihydro-1H-indol-2-yl]-1H-imidazole-4-carboxylic acid (compound 138).

Example B.21

To compound 145 (0.00097 mole), dissolved in ethanol (5 ml), was added several drops of 21% NaOEt in ethanol. The mixture was allowed to stir at room temperature under argon. An additional 2 drops of 21% NaOEt in ethanol were added after 30 minutes. An additional 2 drops of 21% NaOEt in ethanol were added after 16 hours. After 30 minutes the mixture was concentrated and partitioned between water and DCM. The aqueous layer was washed with additional DCM. The combined organics were washed with water, dried, and concentrated, yielding 0.193 g (66%) of [2S-[1(R*),2R*]]-2,3-dihydro-α-methyl-β-oxo-2-(4-propyl-1H-imidazol-2-yl)-1H-indole-1-ethanol (compound 146).

Compound 148 was prepared analogously starting from compound 147.

Example B.22

To a suspension of compound 58 (0.0019 mole) in acetonitrile (15 ml) was added acetic acid, anhydride (0.074 mole). Stirred at room temperature under argon for 4 hours. An additional 1.0 ml of acetic acid, anhydride was added, and the reaction was stirred overnight. After stirring 6 hours more, the reaction was complete. The mixture was concentrated and the residue partitioned between saturated NaHCO$_3$ and chloroform. The organic layer was dried and concentrated. The residue was purified by column chromatography. The desired fractions were combined, triturated in ether and collected. yielding 0.37 g of 1-[[1-[(4-chlorophenyl)acetyl]-4-(3-methoxyphenyl)-4-piperidinyl]methyl]-1,3-dihydro-2H-benzimidazol-2-one (compound 149).

Example B.23

A solution of compound 149 (0.0012 mole) and THF (200 ml) was placed inside of a photochemical reactor and irradiated with UV light for 14 hours. The mixture was then allowed to sit at room temperature under nitrogen for 2 days. The mixture was concentrated. The concentrate was purified on Biotage column, eluting with 1:9 THF in DCM, yielding 0.077 g of 1-[2-(1-acetyl-2,3-dihydro-1H-indol-2-yl)-5-propyl-1H-imidazol-4-yl]-ethanone (compound 150).

Example B.24

Compound 13 (0.00106 mole) dissolved in 10 ml of THF was treated at room temperature with BH$_3$.THF (19 ml), which was a solution in THF. The solution was then placed in an oil bath and heated to 60° C. overnight. After cooling to 0° C., the solution was carefully treated with 15 ml of 3N HCl. The reaction was then warmed to room temperature and stirred for 4 hours. The mixture was then recooled to 0° C. and basified with 12 ml of 3N NaOH, then completion of basification was done with solid Na$_2$CO$_3$. The layers were separated and the aqueous was rewashed with chloroform. The organics were combined, a small amount of aqueous separated, and the organic dried over Na$_2$SO$_4$. The mixture was filtered, and the filtrate concentrated under reduced pressure. The residue was submitted for preparative liquid chromatography, yielding 0.33 g of [2S-[1(R*),2R*]]-2-(4-ethyl-1H-imidazol-2-yl)-2,3-dihydro-α-methyl-1H-indole-1-ethanamine trifluoroacetate (1:1) (compound 127).

Example B.25

3-amino-4-(4-hydroxy-phenyl)-1-[3-(4-phenyl-1H-imidazol-2-yl)-3,4-dihydro-1-H-isoquinolin-2-yl]-butan-1-one (compound 155)

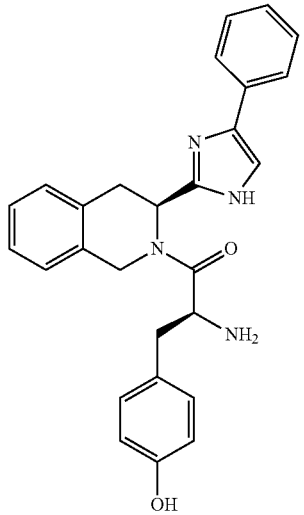

TFA (4 mL) was cooled to about 0° C. and then the product prepared in Example A.15 (1.10 g, 1.85 mmol) was added. The reaction mixture sat for about 0.5 hours. Excess TFA was then removed under a stream of N$_2$ to yield a brown oil. The oil was purified via preparative HPLC to yield the title compound as a white solid.

Measured MW (MH$^+$): 439

Example B.26

2-amino-3-(4-hydroxy-benzyl)-1-[3-(5-methyl-4-phenyl-imidazol-2-yl)-3,4-dihydro-1H-isoquinolin-2-yl]-propan-1-one (compound 153)

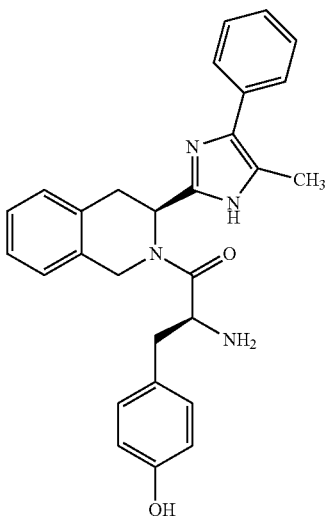

To a solution of TFA (4 mL) cooled to about 0° C. was added the compound prepared in Example A.18 (0.24 g, 0.4 mmol) and the reaction mixture stirred for about 20 minutes. The reaction mixture was then removed from the ice bath and allowed to warm to room temperature. Excess TFA was removed under a stream of $N_2$ to yield crude product. This material was purified via preparative HPLC to yield the title compound as a white solid.

Measured MW (MH+): 453

Table F-1 lists the compounds that were prepared according to one of the above Examples. The following abbreviations were used in the tables: .$C_2HF_3O_2$ stands for the trifluoroacetate salt, .$2C_2H_2O_4$ stands for the ethanedioate salt, and .$C_{10}H_8O_3S$ stands for the 2-naphthalenesulfonate salt. Said Table F-1 lists the structure of the compounds, the Example number according to which these compounds have been prepared, the salt form, the stereochemical designation and the melting point (if measured).

TABLE F-1

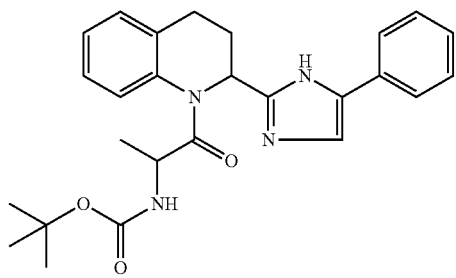

Co. No. 1; Ex. B.1

TABLE F-1-continued

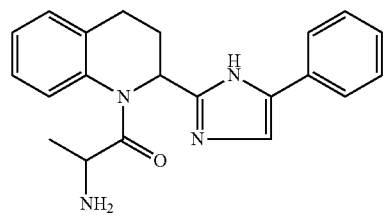

Co. No. 2; Ex. B.5

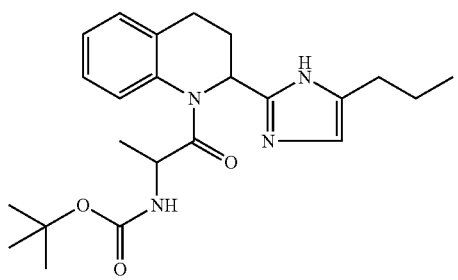

Co. No. 3; Ex. B.1;
[2R-[1(S*),2R*]] +
[2S-(1(R*),2R*]]

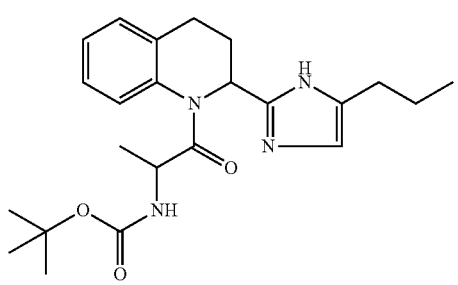

Co. No. 4; Ex. B.1;
[1(S),2A]

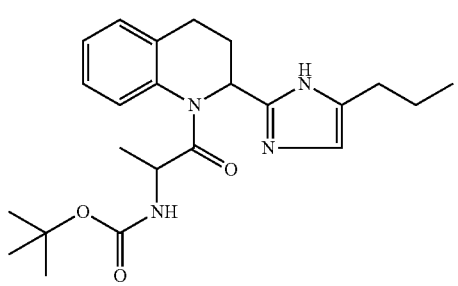

Co. No. 5; Ex. B.1;
[1(S),2B]

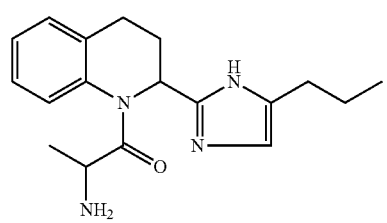

Co. No. 6, Ex. B.5; [1(S),2A]

TABLE F-1-continued
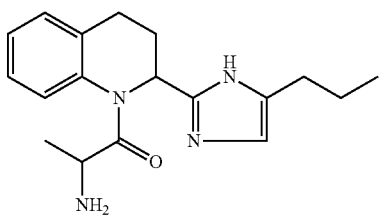
Co. No. 7; Ex. B.5;
[1(S),2B]
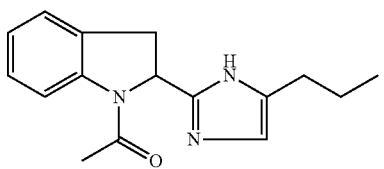
Co. No. 8; Ex. B.2; (S);
mp. 174-175° C.
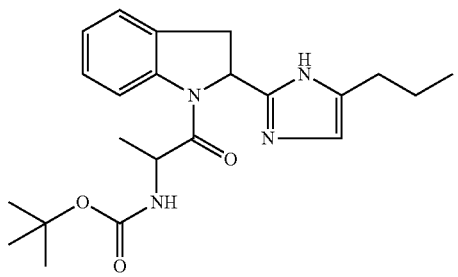
Co. No. 9; Ex. B.1;
[2S-[1(R*),2R*]]
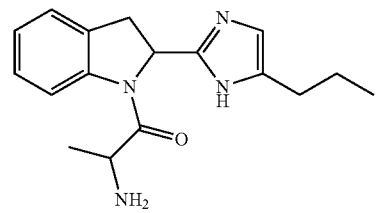
Co. No. 10; Ex. B.5;
[2S-[1(R*),2R*]]
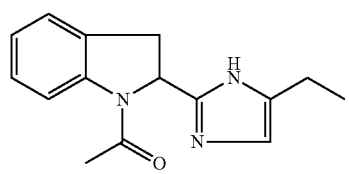
Co. No. 11; Ex. B.2; (S);
mp. 136-139° C.
TABLE F-1-continued
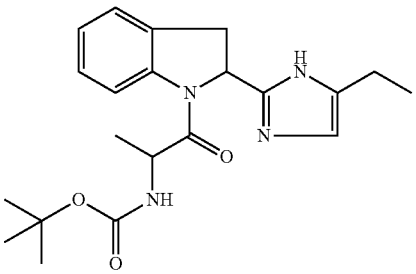
Co. No. 12; Ex. B.1;
[2S-[1(R*),2R*]]
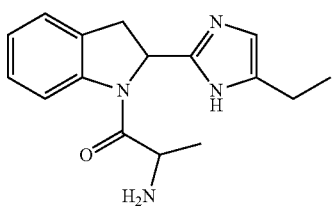
Co. No. 13; Ex. B.5;
[2S-[1(R*),2R*]];
mp. 116-118° C.
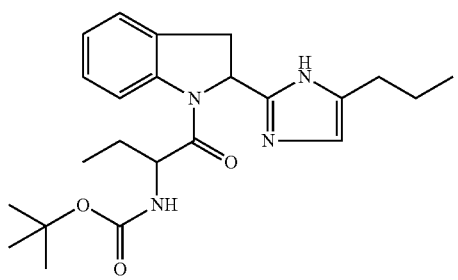
Co. No. 14; Ex. B.1;
[2S-[1(R*),2R*]]
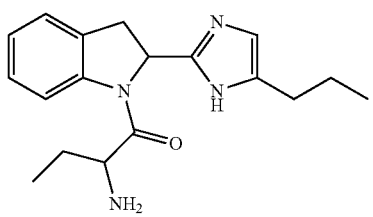
Co. No. 15; Ex. B.5;
·2HCl·2H₂O
[2S-[1(R*),2R*]];
mp. 132-140° C.
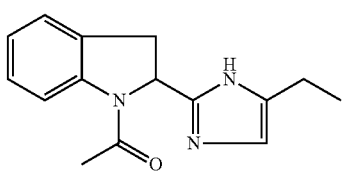
Co. No. 16; Ex. B.2

TABLE F-1-continued
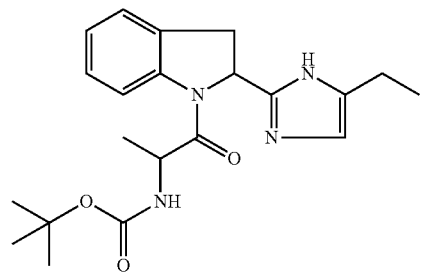
Co. No. 17; Ex. B.1;
[2R-[1(S*),2R*]];
mp. 76-79° C.
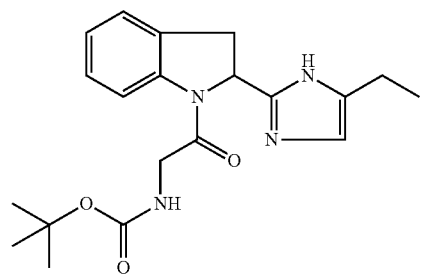
Co. No. 18; Ex. B.1;
mp. 198-199° C.
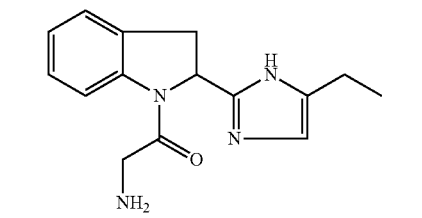
Co. No. 19; Ex. B.5;
mp. 184-186° C.
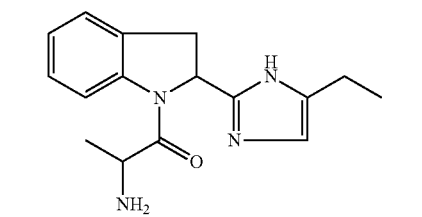
Co. No. 20; Ex. B.5; •H$_2$O
[2R-[1(S*),2R*]];
mp. 73-74° C.
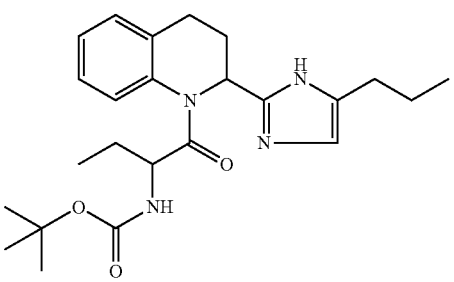
Co. No. 21; Ex. B.1;
[2R-[1(S*),2R*]] +
[2S-[1(R*),2R*]]
TABLE F-1-continued
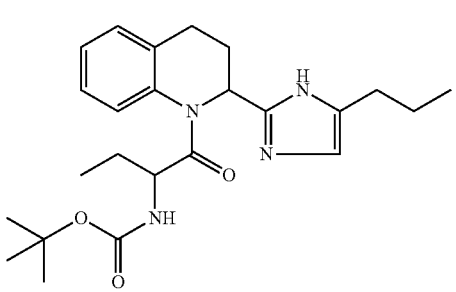
Co. No. 22; Ex. B.1;
[1(S),2A]
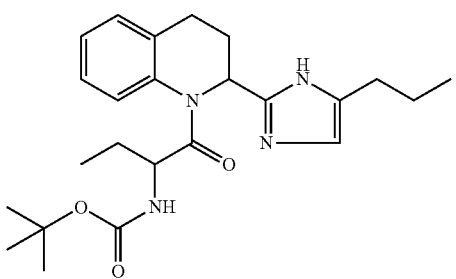
Co. No. 23; Ex. B.1;
[1(S),2B]
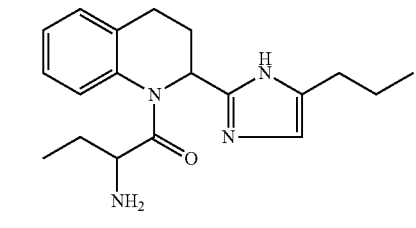
Co. No. 24; Ex. B.5;
•2C$_2$H$_2$O$_4$; [1(S),2A];
mp. >90° C.
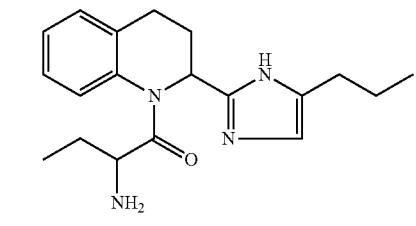
Co. No. 25; Ex. B.5;
•2HCl•2H$_2$O [1(S),2B];
mp. >100° C.
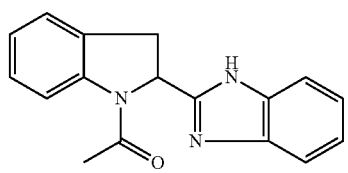
Co. No. 26; Ex. B.2; (S);
mp. 208-210° C.

TABLE F-1-continued
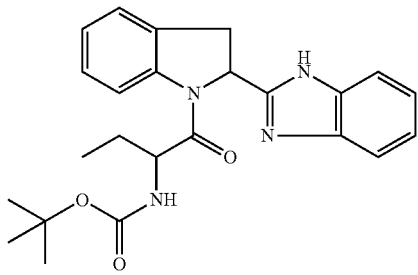
Co. No. 27; Ex. B.4;
[S-[1(R*),R*];
mp. 107-109° C.
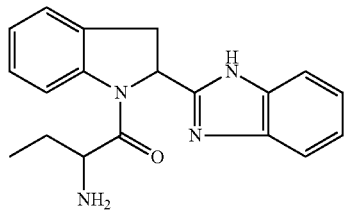
Co. No. 28; Ex. B.5; •3HCl;
[S-[1(R*),R*]];
mp. 240-242° C.
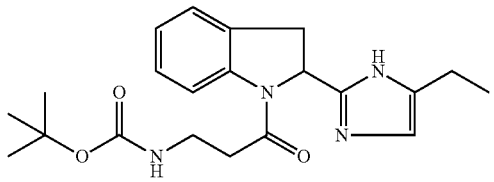
Co. No. 29; Ex. B.4;
mp. 170-171° C.
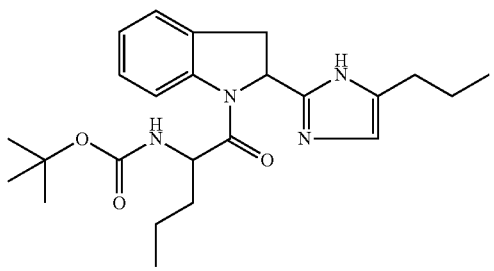
Co. No. 30; Ex. B.4;
•C$_2$HF$_3$O$_2$; [S-(R*,R*)];
mp. 173-175° C.
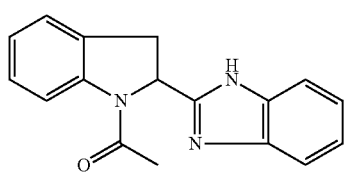
Co. No. 31; Ex. B.2;
mp. 261-262° C.
TABLE F-1-continued
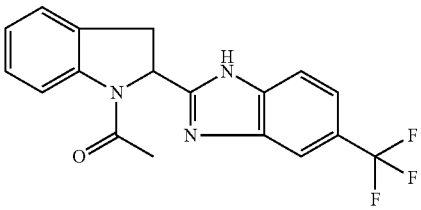
Co. No. 32; Ex. B.2;
mp. 256-257° C.
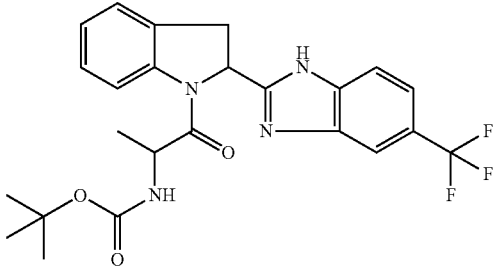
Co. No. 33; Ex. B.1;
•C$_2$HF$_3$O$_2$; [R-(R*,S*)]
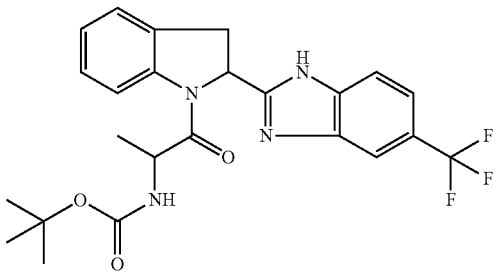
Co. No. 34; Ex. B.1;
•C$_2$HF$_3$O$_2$; [S-(R*,R*)]
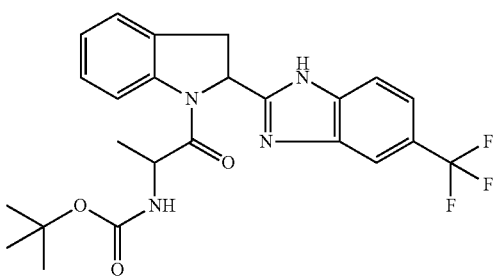
Co. No. 35; Ex. B.1;
•C$_2$HF$_3$O$_2$;
[R-(R*,S*)] + [S-(R*,R*)]
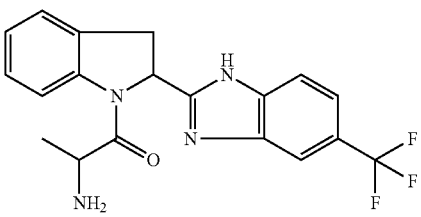
Co. No. 36; Ex. B.5;
•2C$_2$HF$_3$O$_2$; [S-(R*R*)]

TABLE F-1-continued
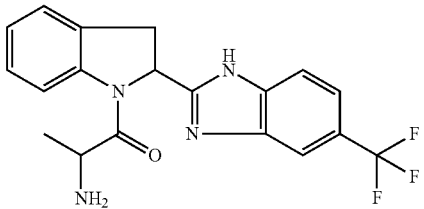
Co. No. 37; Ex. B.5;
•2C2HF3O2;
[R-(R*,S*)] + [S-(R*,R*)]
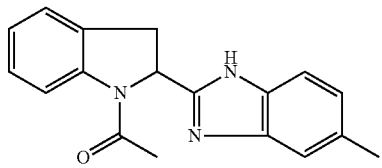
Co. No. 38; Ex. B.2;
mp. 214-216° C.
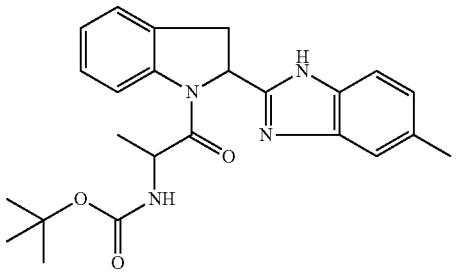
Co. No. 39; Ex. B.1; [1(S)];
mp. 137-138° C.
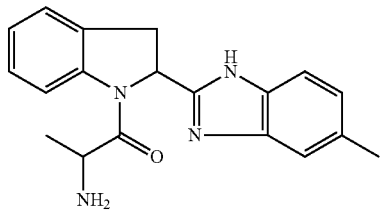
Co. No. 40; Ex. B.5; [1(S)];
mp. 198-203° C.
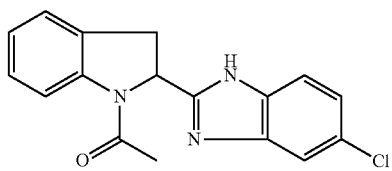
Co. No. 41; Ex. B.2;
mp. 221-222° C.
TABLE F-1-continued
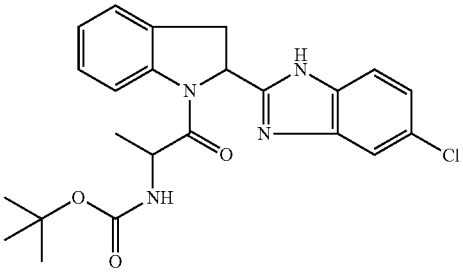
Co. No. 42; Ex. B.1;
•2C2HF3O2; [R-(R*,S*)]
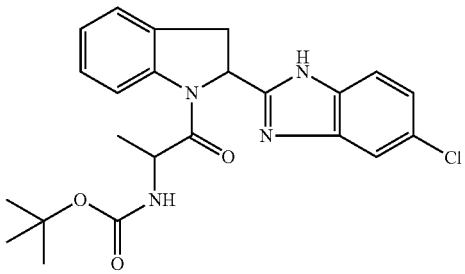
Co. No. 43; Ex. B.1;
•C2HF3O2; [S-(R*,R*)]
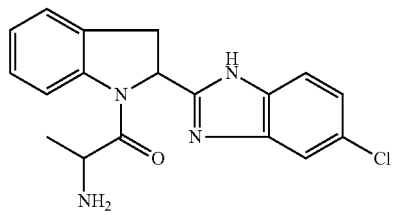
Co. No. 44; Ex. B.5;
•3C2HF3O2; [S-(R*,R*)]
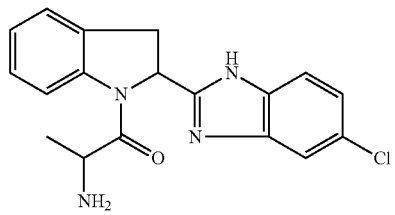
Co. No. 45; Ex. B.5;
•2C2HF3O2;
[R-(R*,S*)] + [S-(R*,R*)]
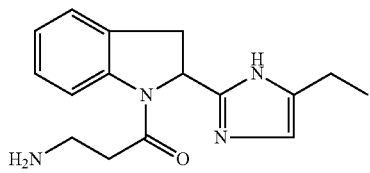
Co. No. 46; Ex. B.5;
mp. 158-160° C.

TABLE F-1-continued
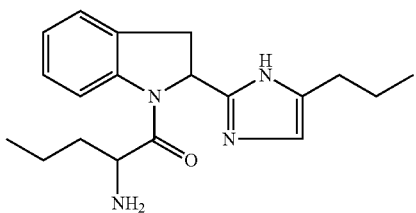
Co. No. 47; Ex. B.5;
•2C₂H₂O₄; [S-(R*,R*)];
mp. 135-137° C.
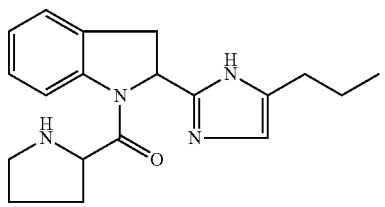
Co. No. 48; Ex. B.5;
•2HCl•3H₂O; [S-(R*,R*)];
mp. 85-87° C.
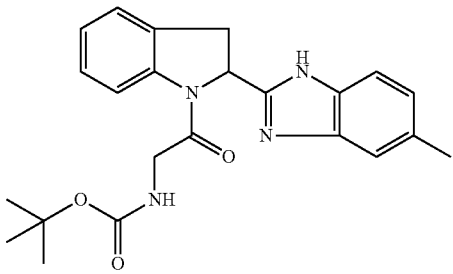
Co. No. 49; Ex. B.4;
•H₂O•C₂HF₃O₂; mp.
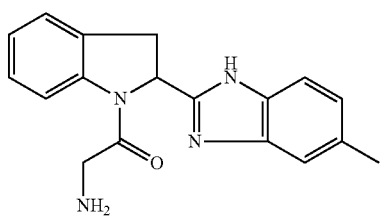
Co. No. 50; Ex. B.5;
mp. 116-118° C.
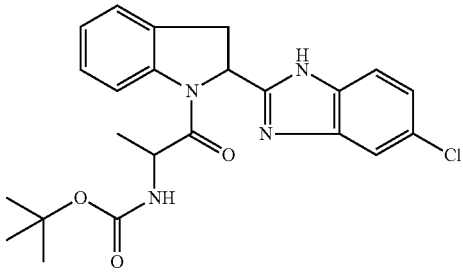
Co. No. 51; Ex. B.1;
•C₂HF₃O₂;
[R-(R*,S*)] + [S-(R*,R*)]
TABLE F-1-continued
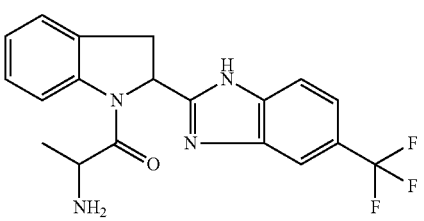
Co. No. 52; Ex. B.5;
•2C₂HF₃O₂; [R-(R*,S*)]
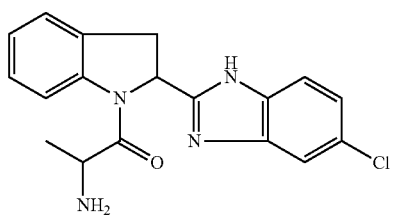
Co. No. 53; Ex. B.5;
•H₂O•2C₂HF₃O₂;
[R-(R*,S*)]
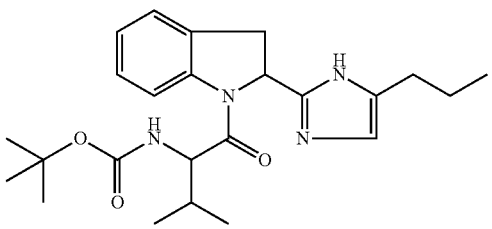
Co. No. 54; Ex. B.4;
•C₂HF₃O₂; [S-(R*,R*)];
mp. 66-68° C.
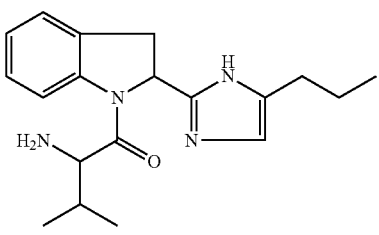
Co. No. 55; Ex. B.5;
•C₁₀H₈O₃S•H₂O;
[S-(R*,R*)]; mp. 195-197° C.
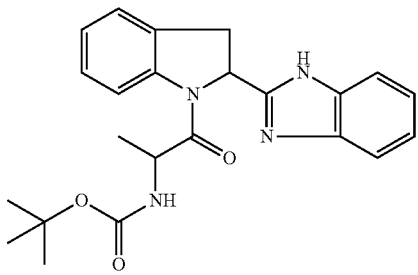
Co. No. 56; Ex. B.1;
[S-(R*,R*)]; mp. 76-78° C.

TABLE F-1-continued
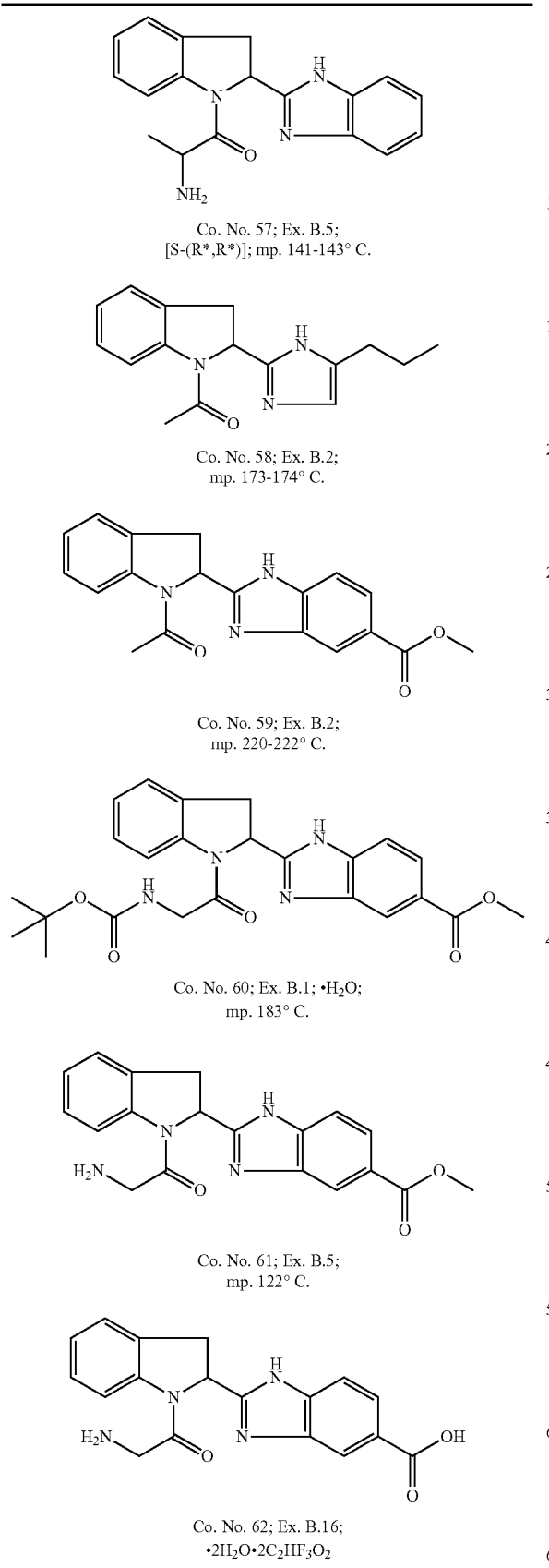
Co. No. 57; Ex. B.5;
[S-(R*,R*)]; mp. 141-143° C.
Co. No. 58; Ex. B.2;
mp. 173-174° C.
Co. No. 59; Ex. B.2;
mp. 220-222° C.
Co. No. 60; Ex. B.1; •H₂O;
mp. 183° C.
Co. No. 61; Ex. B.5;
mp. 122° C.
Co. No. 62; Ex. B.16;
•2H₂O•2C₂HF₃O₂
TABLE F-1-continued
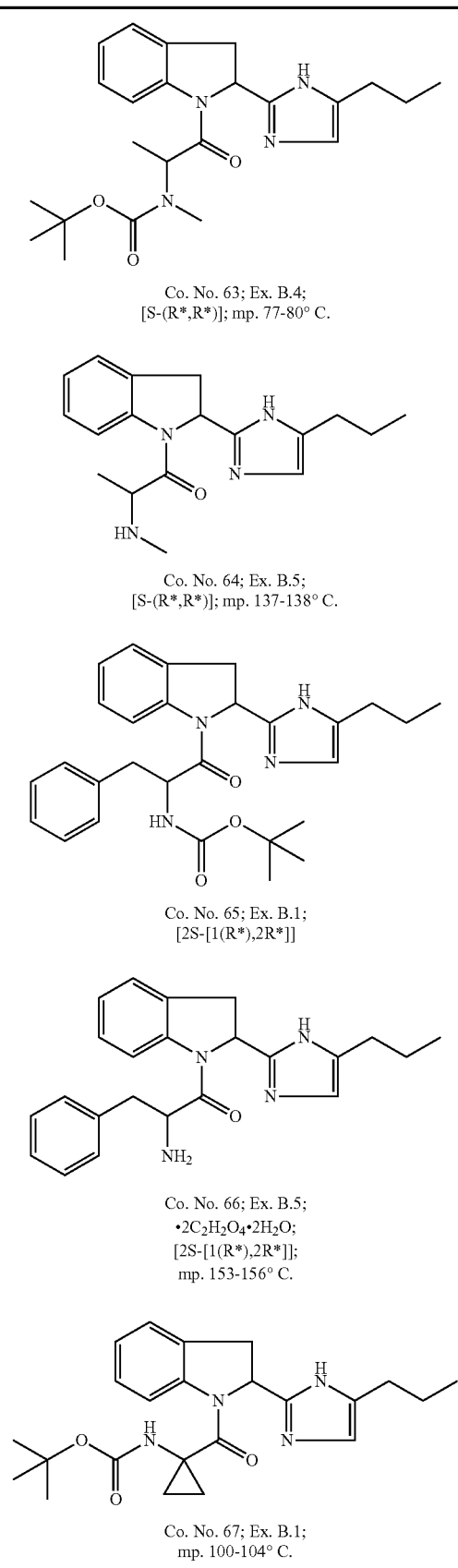
Co. No. 63; Ex. B.4;
[S-(R*,R*)]; mp. 77-80° C.
Co. No. 64; Ex. B.5;
[S-(R*,R*)]; mp. 137-138° C.
Co. No. 65; Ex. B.1;
[2S-[1(R*),2R*]]
Co. No. 66; Ex. B.5;
•2C₂H₂O₄•2H₂O;
[2S-[1(R*),2R*]];
mp. 153-156° C.
Co. No. 67; Ex. B.1;
mp. 100-104° C.

TABLE F-1-continued

Co. No. 68; Ex. B.5;
·HCl·H2O; mp. 152° C.

Co. No. 69; Ex. B.1

Co. No. 70; Ex. B.5; ·H2O;
np. 168-170° C.

Co. No. 71; Ex. B.2; ·2KCl;
mp. 189-191° C.

Co. No. 72; Ex. B.1;
mp. 168° C.

Co. No. 73; Ex. B.5;
·H2O·2C2HF3O2; mp. >300° C.

TABLE F-1-continued

Co. No. 74; Ex. B.2;
mp. 191-192° C.

Co. No. 75; Ex. B.1;
mp. 214-216° C.

Co. No. 76; Ex. B.5;
mp. 158-160° C.

Co. No. 77; Ex. B.11

Co. No. 78; Ex. B.11

TABLE F-1-continued
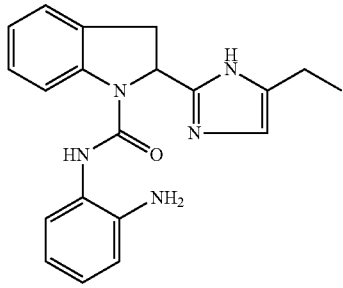
Co. No. 79; Ex. B.12;
•2C₂HF₃O₂
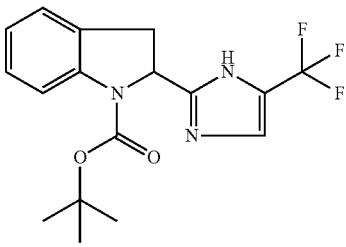
Co. No. 80; Ex. B.3;
mp. 179-181° C.
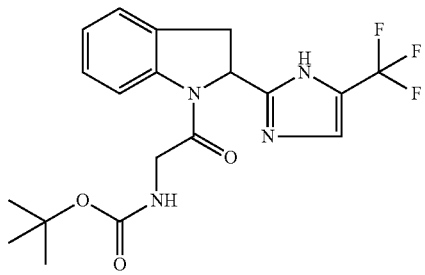
Co. No. 81; Ex. B.1
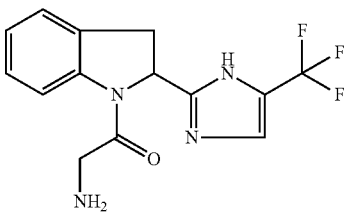
Co. No. 82; Ex. B.5;
mp. 186-188° C.
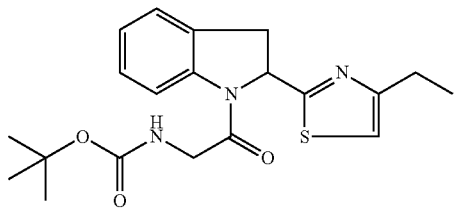
Co. No. 83; Ex. B.1
TABLE F-1-continued
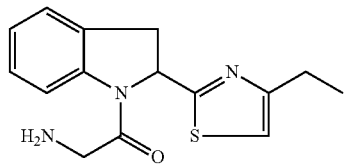
Co. No. 84; Ex. B.5;
•C₄H₄O₄; mp. 173-174° C.
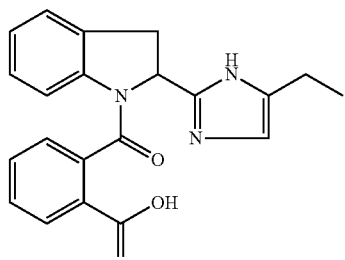
Co. No. 85; Ex. B.10;
•C₂HF₃O₂
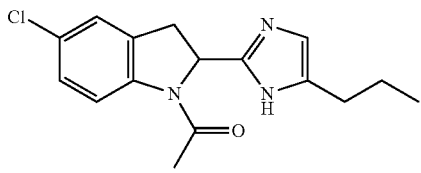
Co. No. 86; Ex. B.2;
mp. 225-226° C.
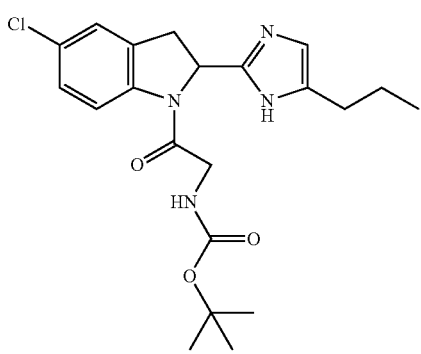
Co. No. 87; Ex. B.4;
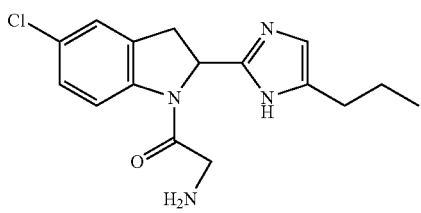
Co. No. 88; Ex. B.5;
mp. 193-195° C.

TABLE F-1-continued
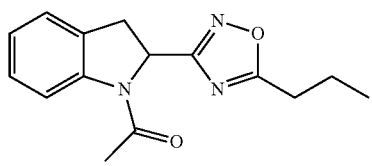
Co. No. 89; Ex. B.8
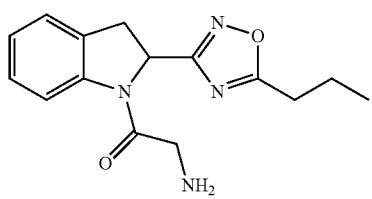
Co. No. 90; Ex. B.9;
•C$_2$HF$_3$O$_2$
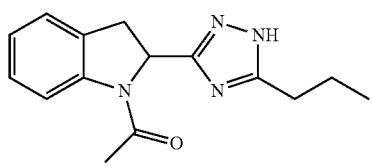
Co. No. 91; Ex. B.6; mp.
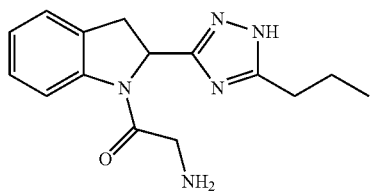
Co. No. 92; Ex. B.7;
•C$_2$HF$_3$O$_2$
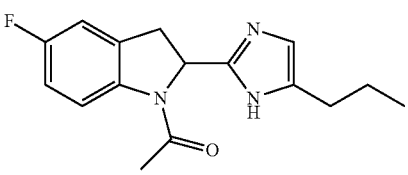
Co. No. 93; Ex. B.2
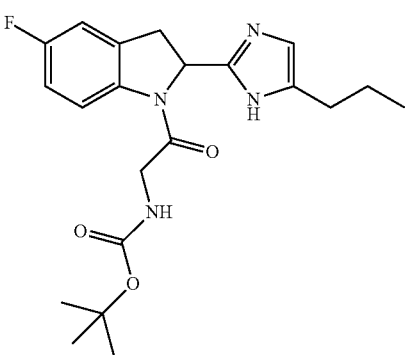
Co. No. 94; Ex. B.1;
•C$_2$HF$_3$O$_2$
TABLE F-1-continued
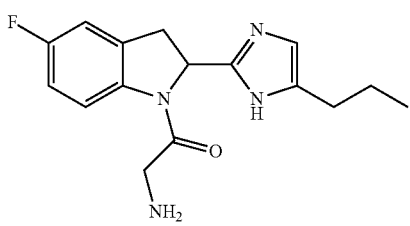
Co. No. 95; Ex. B.5;
•C$_2$HF$_3$O$_2$
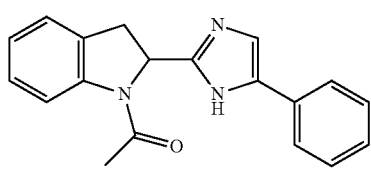
Co. No. 96; Ex. B.2
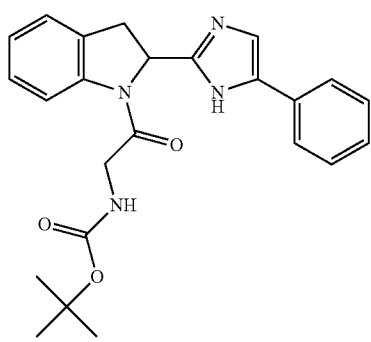
Co. No. 97; Ex. B.4
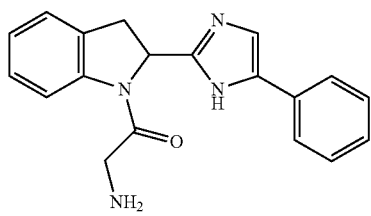
Co. No. 98; Ex. B.5;
mp. 214-215° C.
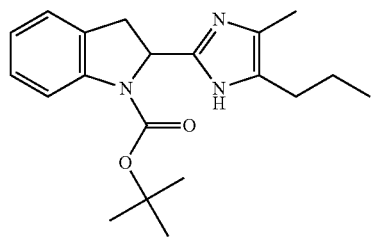
Co. No. 99; Ex. B.3

TABLE F-1-continued
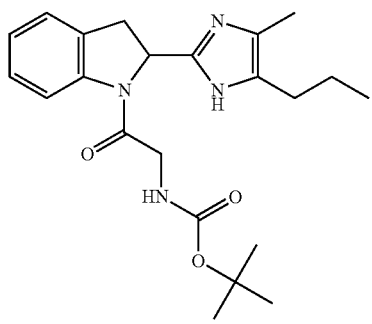
Co. No. 100; Ex. B.1;
mp. 165-167° C.
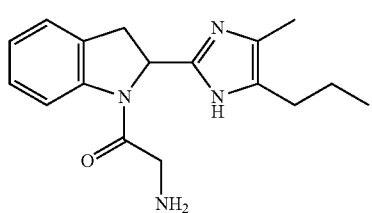
Co. No. 101; Ex. B.5;
mp. 197-198° C.
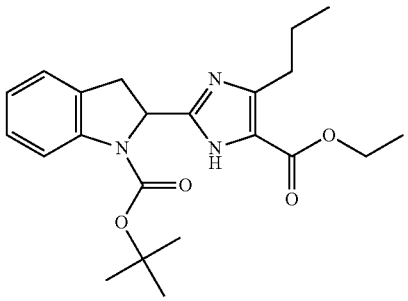
Co. No. 102; Ex. B.3
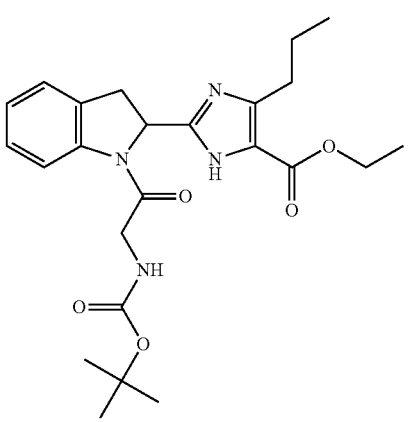
Co. No. 103; Ex. B.4
TABLE F-1-continued
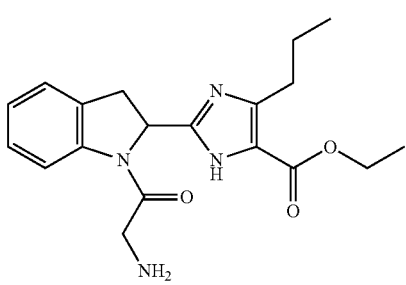
Co. No. 104; Ex. B.5;
·$C_2HF_3O_2$; mp. 102-105° C.
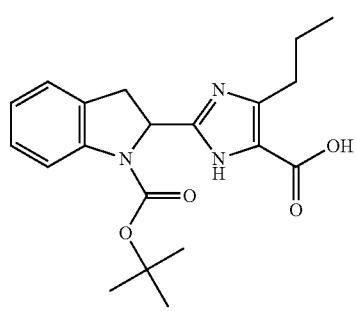
Co. No. 105; Ex. B.17
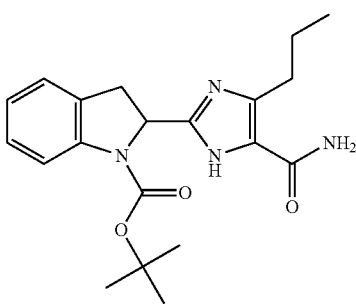
Co. No. 106; Ex. B.18
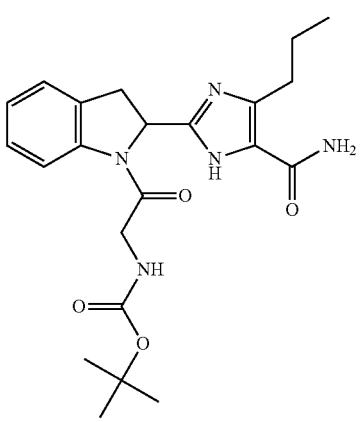
Co. No. 107; Ex. B.1

TABLE F-1-continued
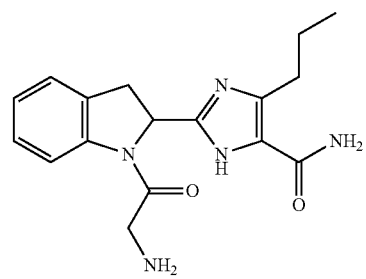
Co. No. 108; Ex. B.5;
•C$_2$HF$_3$O$_2$; mp. 124-131° C.
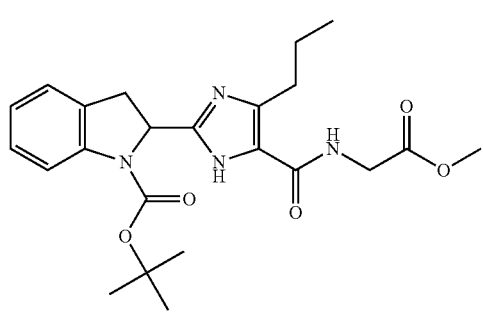
Co. No. 109; Ex. B.19
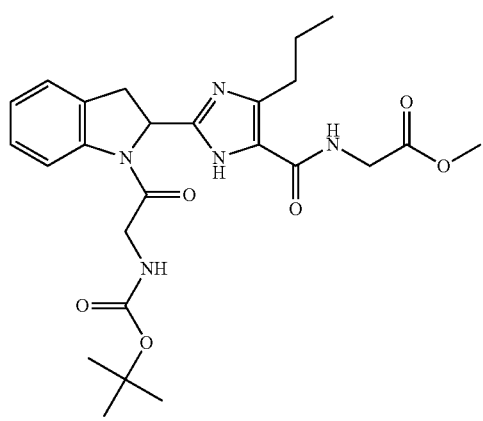
Co. No. 110; Ex. B.1
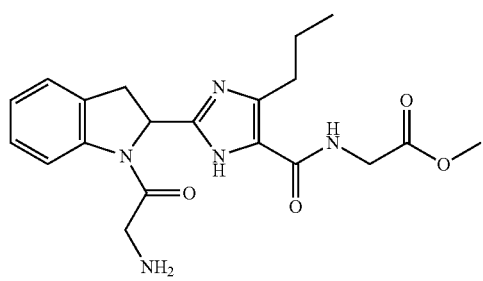
Co. No. 111; Ex. B.5;
•C$_2$HF$_3$O$_2$; mp. 95-99° C.
TABLE F-1-continued
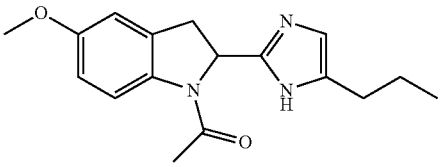
Co. No. 112; Ex. B.2;
mp. 236-237° C.
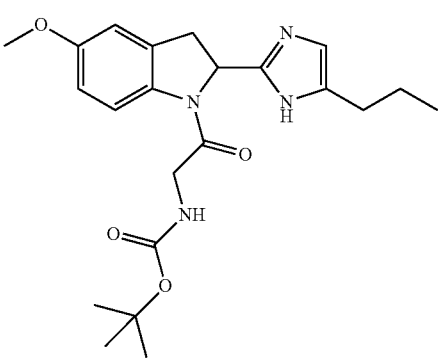
Co. No. 113; Ex. B.1; mp.
184-188° C.
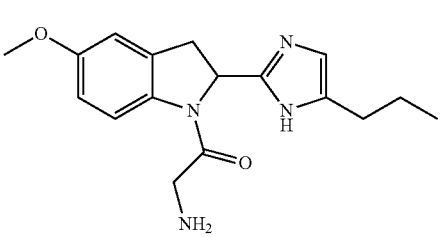
Co. No. 114; Ex. B.5;
•C$_2$HF$_3$O$_2$
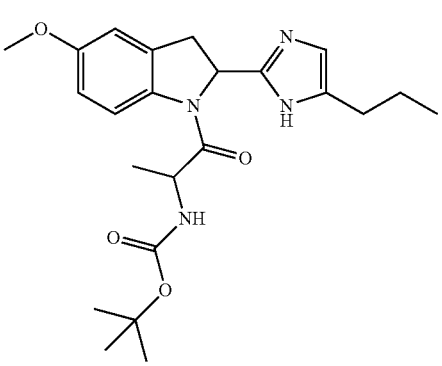
Co. No. 115; Ex. B.1;
•C$_2$HF$_3$O$_2$
[2R-[1(S*),2R*]]

TABLE F-1-continued
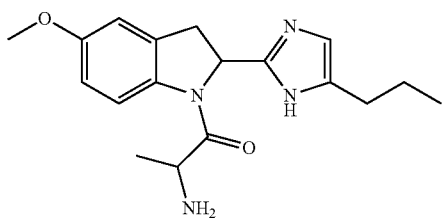
Co. No. 116; Ex. B.5;
•C₂HF₃O₂
[2R-[1(S*),2R*]]
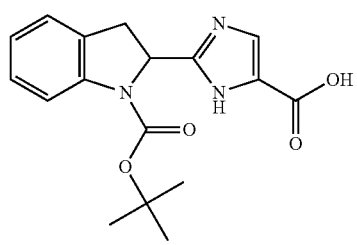
Co. No. 117; Ex. B.14
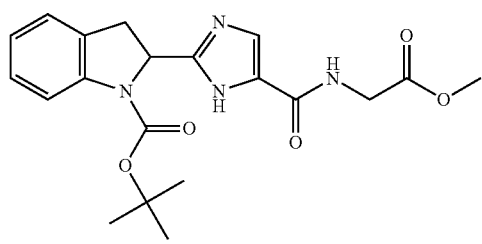
Co. No. 118; Ex. B.15
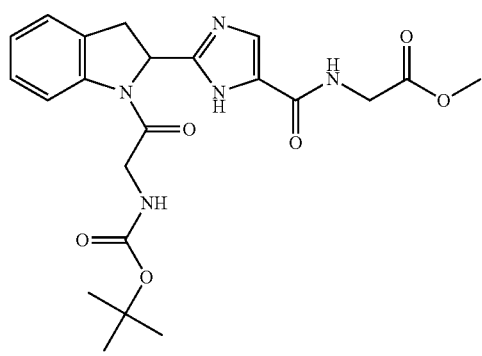
Co. No. 119; Ex. B.1
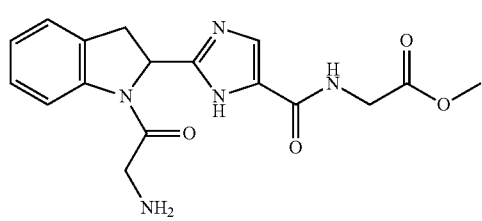
Co. No. 120; Ex. B.5;
•C₂HF₃O₂
TABLE F-1-continued
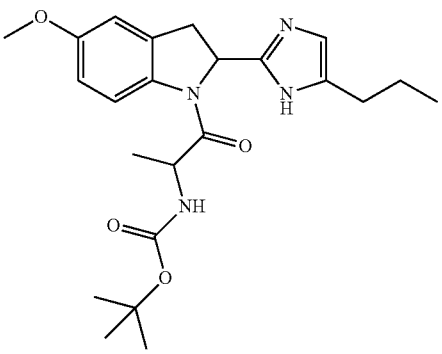
Co. No. 121; Ex. B.1;
•C₂HF₃O₂
[2S-[1(R*),2R*]]
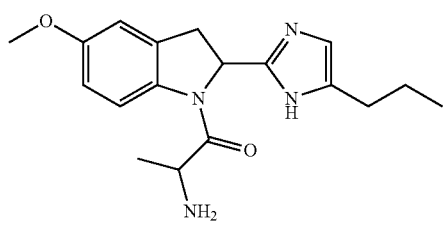
Co. No. 122; Ex. B.5;
•C₂HF₃O₂
[2S-[1(R*),2R*]]
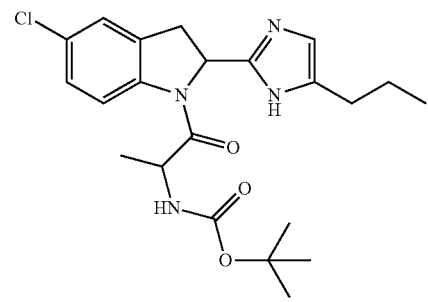
Co. No. 123; Ex. B.1;
•C₂HF₃O₂
[2R-[1(S*),2R*]]
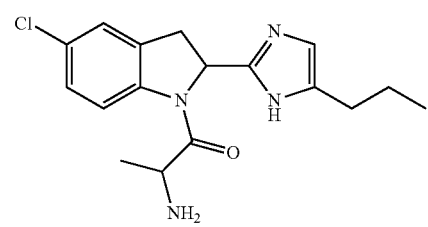
Co. No. 124; Ex. B.5;
•C₂HF₃O₂
[2R-[1(S*),2R*]]

TABLE F-1-continued
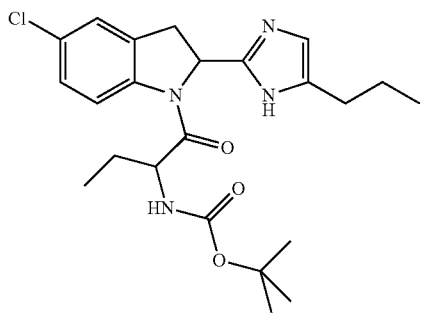
Co. No. 125; Ex. B.4;
•C₂HF₃O₂
[2R-[1(S*),2R*]]
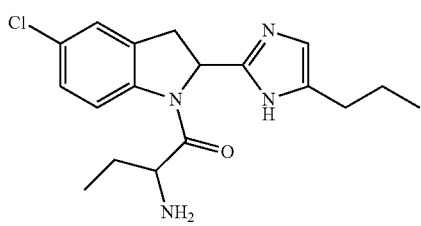
Co. No. 126; Ex. B.5;
•C₂HF₃O₂
[2R-[1(S*),2R*]]
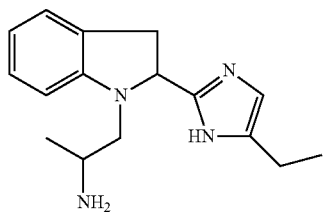
Co. No. 127; Ex. B.24;
•C₂HF₃O₂;
[2S-[1(R*),2R*]]
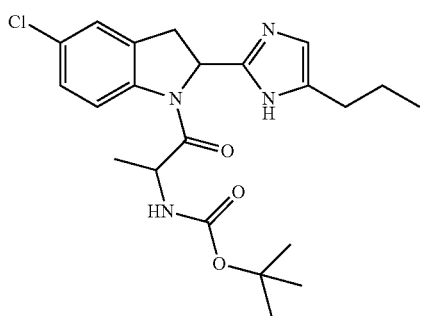
Co. No. 128; Ex. B.1;
•C₂HF₃O₂;
[2S-[1(R*),2R*]]
TABLE F-1-continued
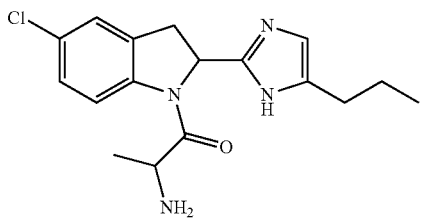
Co. No. 129; Ex. B.5;
•C₂HF₃O₂;
[2S-[1(R*),2R*]]
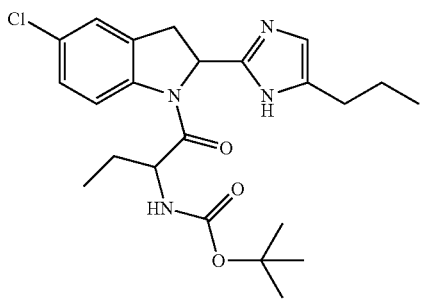
Co. No. 130; Ex. B.4;
•C₂HF₃O₂;
[2S-[1(R*),2R*]]
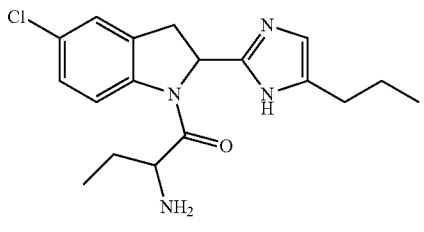
Co. No. 131; Ex. B.5; •HCl
[2S-[1(R*),2R*]];
mp. 235-240° C.
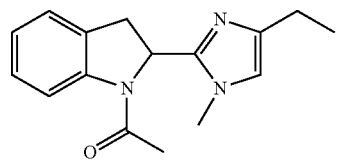
Co. No. 132; Ex. B.13
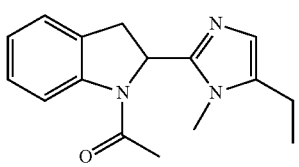
Co. No. 123; Ex. B.13

TABLE F-1-continued
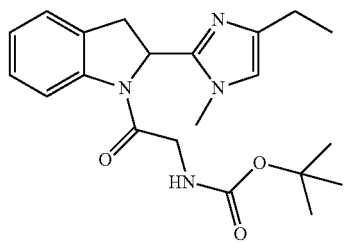
Co. No. 134; Ex. B.1
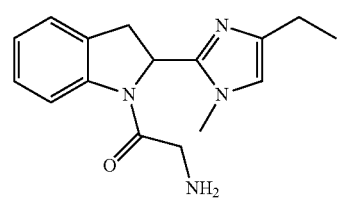
Co. No. 135; Ex. B.5;
mp. 115-117° C.
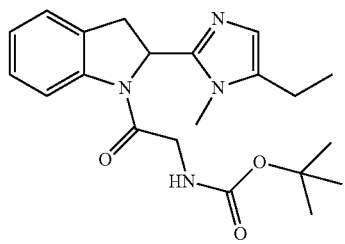
Co. No. 136; Ex. B.1
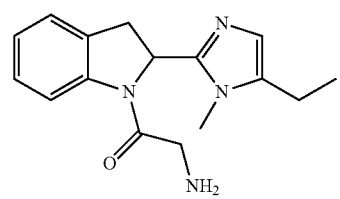
Co. No. 137; Ex. B.5;
mp. 107-109° C.
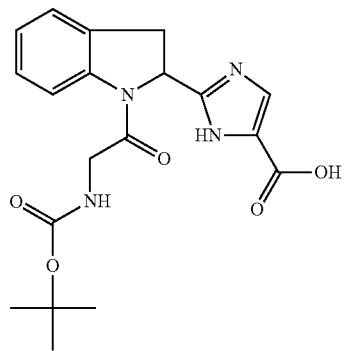
Co. No. 138; Ex. B.20
TABLE F-1-continued
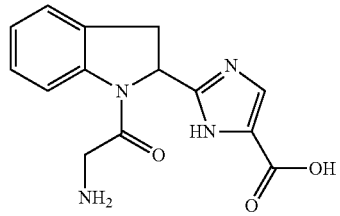
Co. No. 139; Ex. B.5;
•C₂HF₃O₂
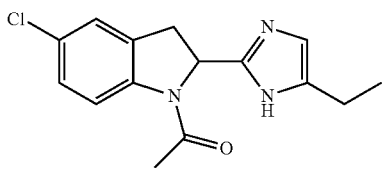
Co. No. 140; Ex. B.2
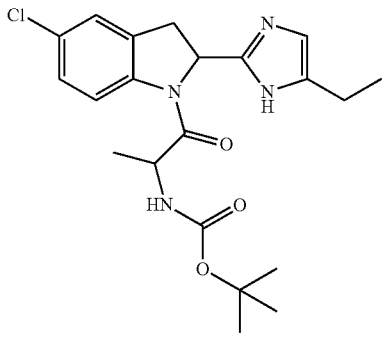
Co. No. 141; Ex. B.1;
•C₂HF₃O₂;
[2R-[1(S*),2R*]]
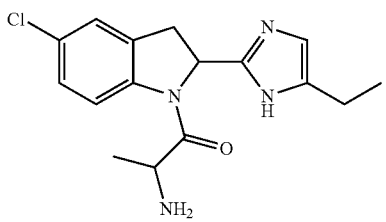
Co. No. 142; Ex. B.5;
[2R-[1(S*),2R*]]
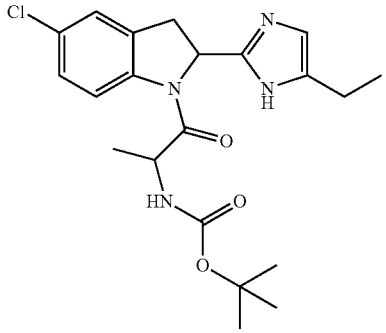
Co. No. 143; Ex. B.1;
•C₂HF₃O₂
[2S-[1(R*),2R*]]

TABLE F-1-continued
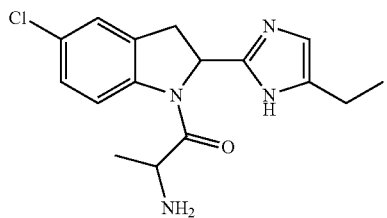
Co. No. 144; Ex. B.5;
[2S-[1(R*),2R*]]
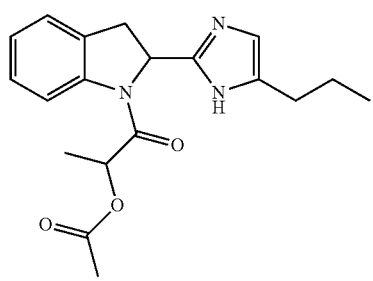
Co. No. 145; Ex. B.1;
[2S-[1(R*),2R*]]
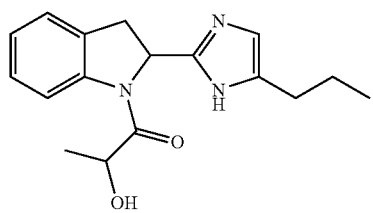
Co. No. 146; Ex. B.21;
[2S-[1(R*),2R*]]
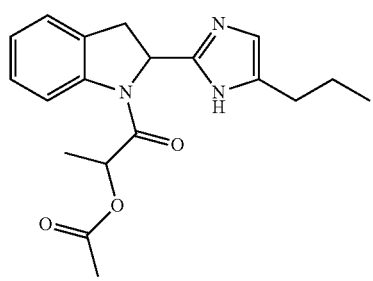
Co. No. 147; Ex. B.1;
[2R-[1(S*),2R*]]
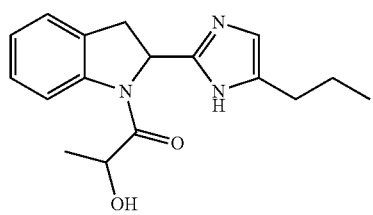
Co. No. 148; Ex. B.21;
[2R-[1(S*),2R*]]
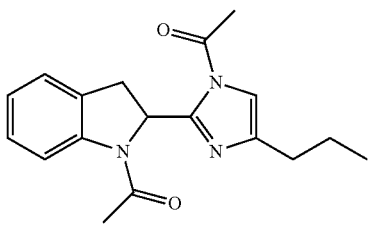
Co. No. 149; Ex. B.22
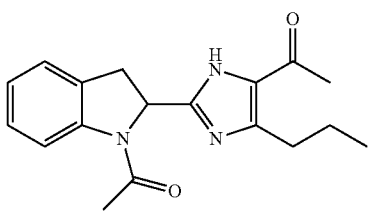
Co. No. 150; Ex. B.23
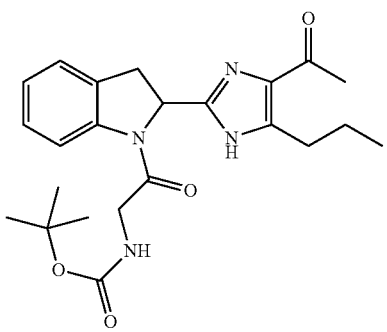
Co. No. 151; Ex. B.1
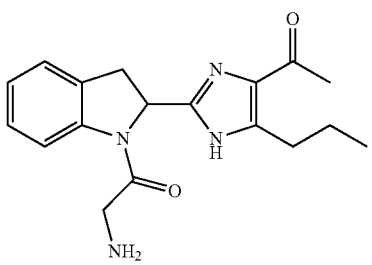
Co. No. 152; Ex. B.5;
·C$_2$HF$_3$O$_2$
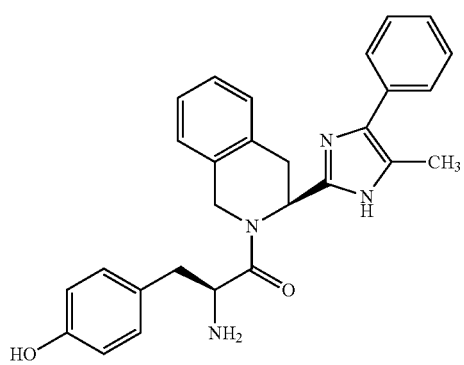
Co. No. 153; Ex. B.26

TABLE F-1-continued
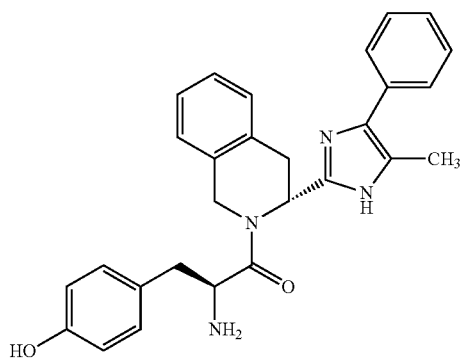
Co. No. 154; Ex. B.26
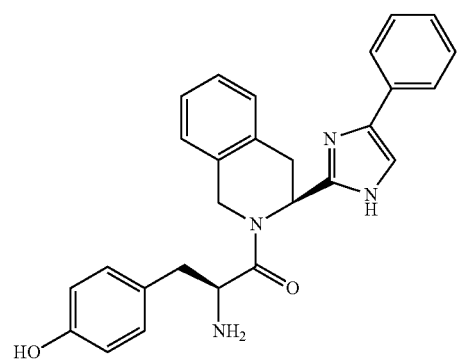
Co. No. 155; Ex. B.25
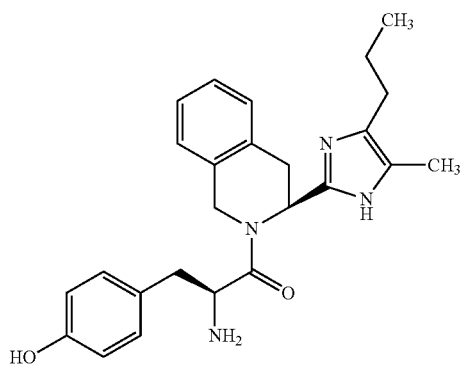
Co. No. 156; Ex. B.26
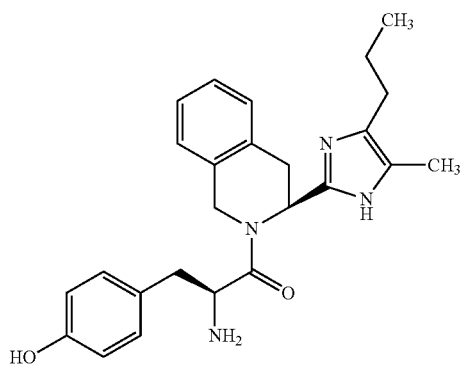
Co. No. 157; Ex. B.26
TABLE F-1-continued
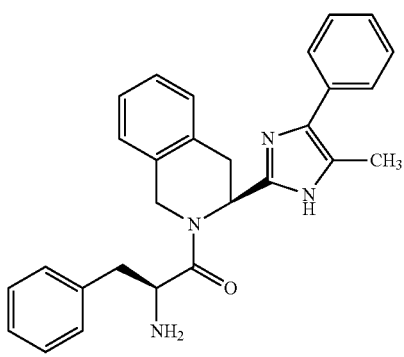
Co. No. 158; Ex. B.26
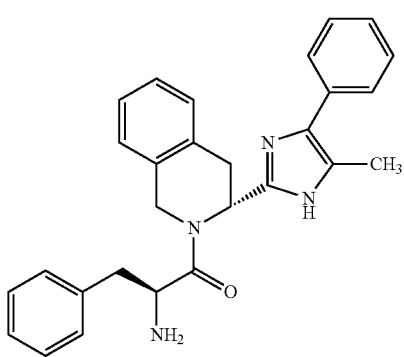
Co. No. 159; Ex. B.26
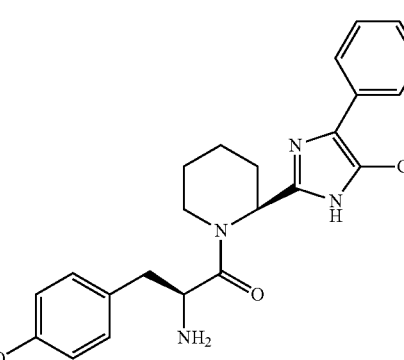
Co. No. 160; Ex. B.26
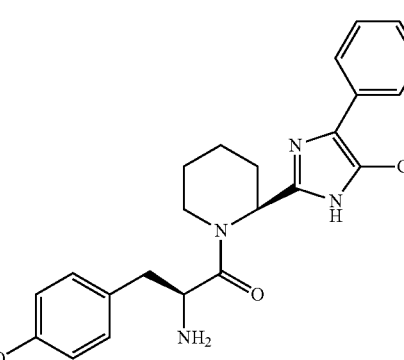
Co. No. 161; Ex. B.25

TABLE F-1-continued
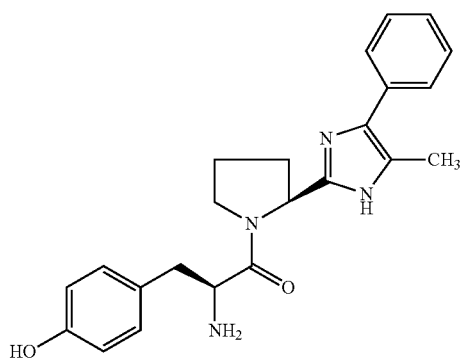
Co. No. 162; Ex. B.26
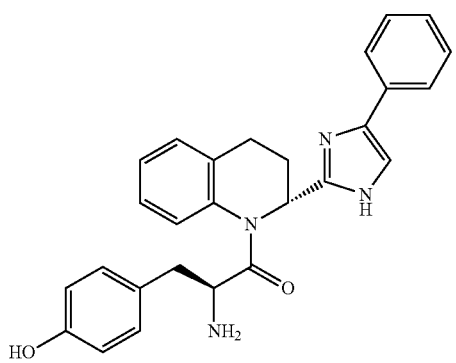
Co. No. 166; Ex. B.25
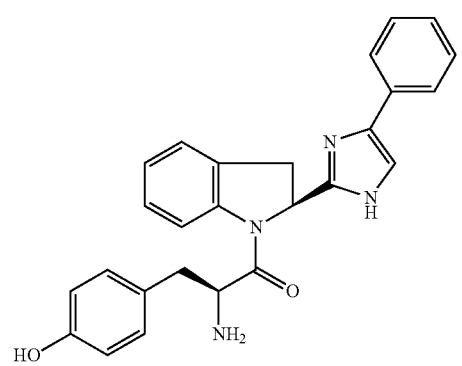
Co. No. 163; Ex. B.25
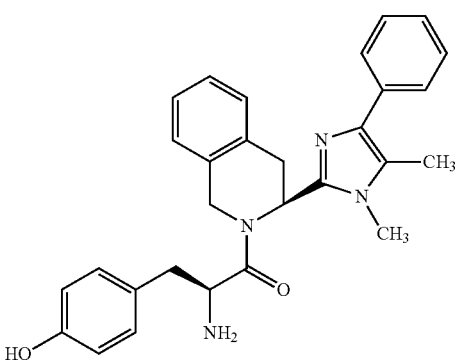
Co. No. 167; Ex. B.25
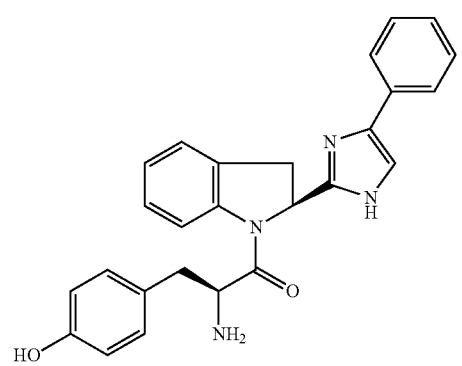
Co. No. 164; Ex. B.25
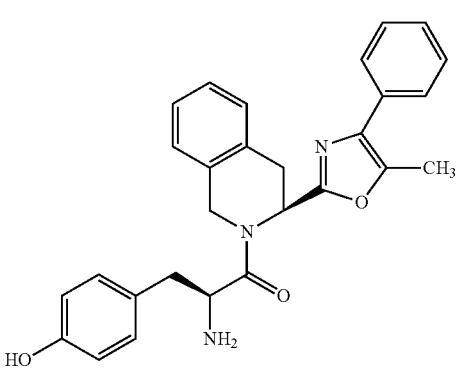
Co. No. 168; Ex. B.25
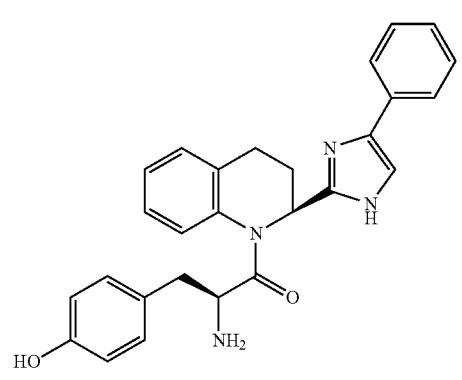
Co. No. 165; Ex. B.25
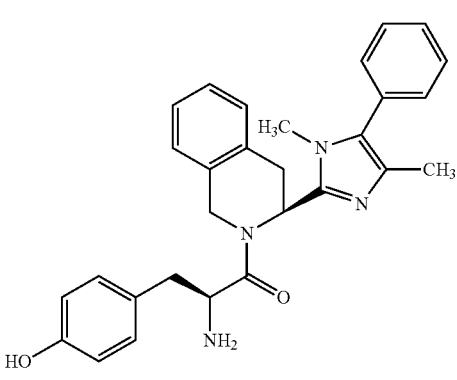
Co. No. 169; Ex. B.25

TABLE F-1-continued
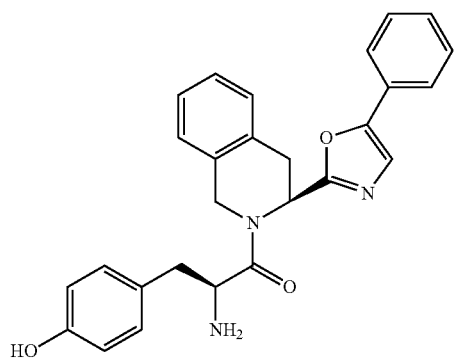
Co. No. 170; Ex. B.25
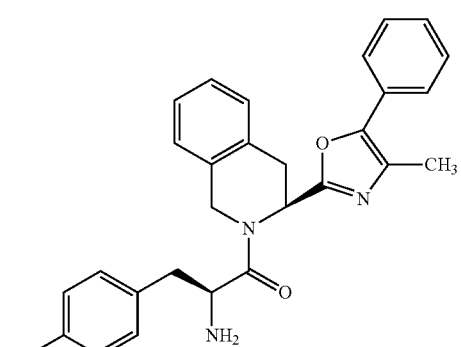
Co. No. 171; Ex. B.25
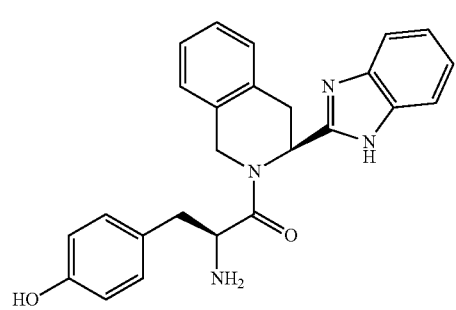
Co. No. 172; Ex. B.25
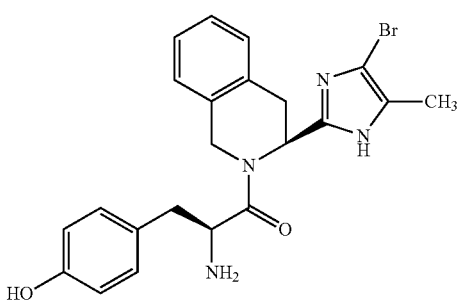
Co. No. 173; Ex. B.26
TABLE F-1-continued
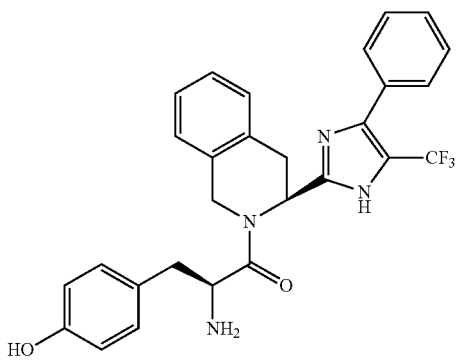
Co. No. 174; Ex. B.26
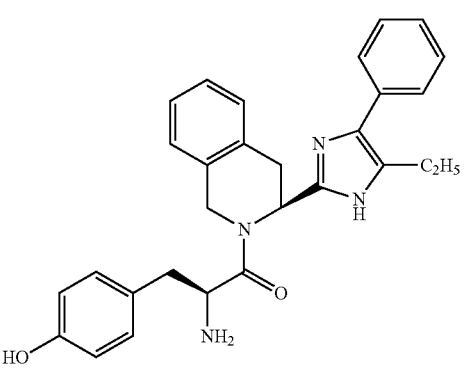
Co. No. 175; Ex. B.26
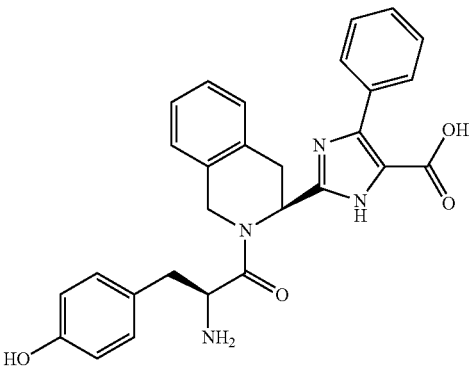
Co. No. 176; Ex. B.26
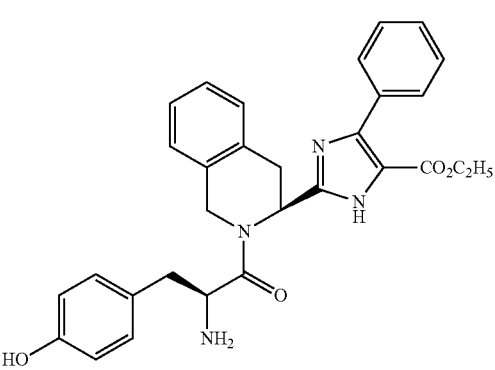
Co. No. 177; Ex. B.26

TABLE F-1-continued

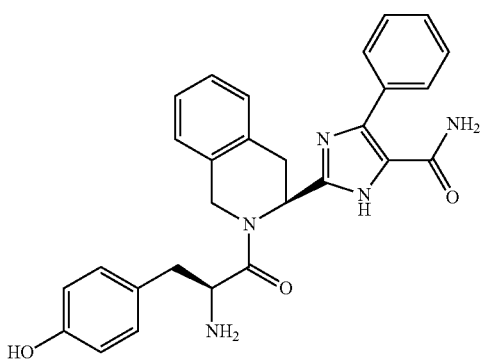

Co. No. 178; Ex. B.26

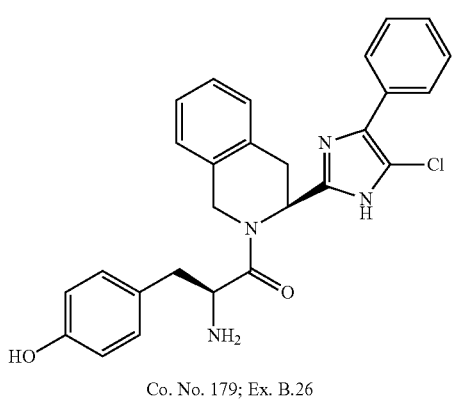

Co. No. 179; Ex. B.26

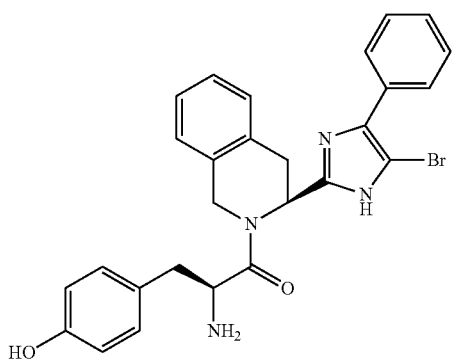

Co. No. 180; Ex. B.26

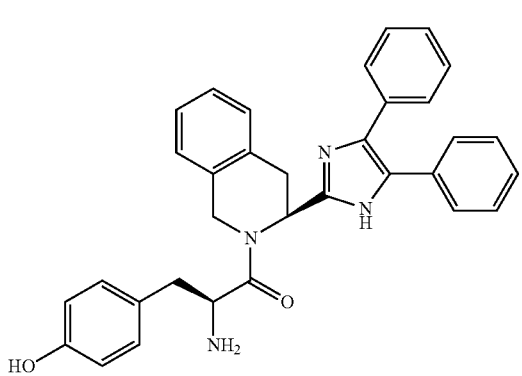

Co. No. 181; Ex. B.26

C. Pharmacological Examples

C.1. Inhibition of Tripeptidyl Peptidase II (TPP II)

The inhibition of TPP II was measured using the procedure as described by C. Rose et al. in Nature, 380, 403-409 (1996).

TPPII activity was evaluated using 15 μM AAF-AMC as a substrate in a 50 mM Potassiumphosphate buffer pH 7.5 with 1 mM DTT and 1 mM EGTA. Compounds were added at a final DMSO concentration of 1%. Fluorescence was measured at 405 nm. The potency of the compounds of formula (I) was expressed as the $IC_{50}$ value, i.e. the concentration needed to provide 50% inhibition.

Compounds 6, 10, 13, 15, 19, 22, 24, 28, 30, 44, 47, 48, 54, 55, 57, 61, 62, 66, 68, 70, 73, 76, 82, 84, 88, 90, 92, 95, 101, 104, 108, 111, 114, 116, 120, 122, 124, 126, 129, 131, 135, 142, and 144 have an $IC_{50}$ value equal to or lower than $1.10^{-5}$ M.

C.2 Rat Brain δ-Opioid Receptor Binding Assay

Male, Wistar rats (150-250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is re-suspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles is determined using Formula 989 scintillation fluid (New England Nuclear, Boston, Mass.) in a scintillation counter.

The data are used to calculate either the % inhibition compared to control binding (when only a single concentration of test compound is evaluated) or a $K_i$ value (when a range of concentrations is tested).

% Inhibition is calculated as follows:

$$\left(1 - \left[\frac{(\text{Test Compound } dpm - \text{Non-specific } dpm)}{(\text{Total } dpm - \text{Non-specific } dpm)}\right]\right) \times 100\%$$

$K_i$ value is calculated using the LIGAND (Munson, P. J. and Rodbard, D., Anal. Biochem. 107: 220-239, 1980) data analysis program.

C.3 Rat Brain μ-Opioid Receptor Binding Assay

Male, Wistar rats (150-250 g, VAF, Charles River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is re-suspended in the same volume of Tris buffer with several brief pulses from a Polytron homogenizer. This particulate preparation is used for the μ-opioid binding assays. Following incubation with the μ-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles is determined using Formula 989 scintillation fluid (New England Nuclear, Boston, Mass.) in a scintillation counter.

The data are used to calculate either the % inhibition compared to control binding (when only a single concentration of test compound is evaluated) or a $K_i$ value (when a range of concentrations is tested).

% Inhibition is calculated as follows:

$$\left(1 - \left[\frac{(\text{Test Compound } dpm - \text{Non-specific } dpm)}{(\text{Total } dpm - \text{Non-specific } dpm)}\right]\right) \times 100\%$$

$K_i$ value was calculated using the LIGAND (Munson, P. J. and Rodbard, D., Anal. Biochem. 107: 220-239, 1980) data analysis program.

The invention claimed is:

1. A compound of formula (I)

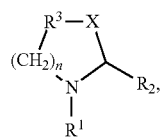

(I)

a stereochemically isomeric form thereof, or a pharmaceutically acceptable addition salt thereof, wherein
n is 0;
X represents —(CR$^4$R$^5$)$_m$— wherein m is 1; R$^4$ and R$^5$ are each independently from each other hydrogen or C$_{1-4}$alkyl;
R$^1$ is C$_{1-6}$alkylcarbonyl optionally substituted with hydroxy;
aminoC$_{1-6}$alkylcarbonyl wherein the C$_{1-6}$alkyl group is optionally substituted with C$_{3-6}$cycloalkyl; mono- and di(C$_{1-4}$alkyl)aminoC$_{1-6}$alkylcarbonyl; aminocarbonyl substituted with aryl; C$_{1-6}$alkylcarbonyloxyC$_{1-6}$alkylcarbonyl; C$_{1-6}$alkyloxycarbonylaminoC$_{1-6}$alkylcarbonyl wherein the amino group is optionally substituted with C$_{1-4}$alkyl; an amino acid bound via the carbonyl group; C$_{1-6}$alkyl substituted with amino; or arylcarbonyl;
R$^2$ is

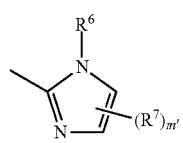

(a-2)

wherein m' is an integer 1 to 2;
R$^6$ is hydrogen or C$_{1-4}$alkyl;
R$^7$ is independently from each other halo; trifluoromethyl; C$_{1-6}$alkyl; phenyl; aminocarbonyl; hydroxycarbonyl; or C$_{1-4}$alkyloxycarbonyl;
R$^3$ is a bivalent radical of formula

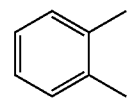

(b-1)

wherein said (b-1) optionally can be substituted with one, two or three substituents each independently selected from halo, hydroxy, C$_{1-6}$alkyl, C$_{1-6}$alkyloxy, nitro, amino, cyano, trifluoromethyl, phenyl, or phenyl substituted with one or two subsitutents each independently selected from halo, hydroxy, cyano, C$_{1-6}$alkyl, C$_{1-6}$alkyloxy, nitro, cyano, and trifluoromethyl;
aryl is phenyl, or phenyl substituted with amino, nitro or hydroxycarbonyl.

2. A compound as claimed in claim 1 wherein n is 0 and R$^3$ is a radical of formula (b-1) optionally substituted with halo or methoxy.

3. A compound as claimed in claim 1 wherein n is 0, R$^3$ is a radical of formula (b-1) optionally substituted with halo or methoxy, and X represents —CH$_2$— or —CH$_2$CH$_2$—.

4. A compound according to claim 1 wherein R$^1$ is C$_{1-6}$alkylcarbonyl, aminoC$_{1-6}$alkylcarbonyl or an amino acid.

5. A pharmaceutical composition comprising a pharmaceutically acceptable carrier and a therapeutically active amount of a compound as claimed in claim 1.

6. A process for preparing a compound of formula (I) wherein
a) an intermediate of formula (II) is reacted with an intermediate of formula (III) in a reaction-inert solvent and, optionally in the presence of a suitable base, thereby yielding compounds of formula (I-a), defined as compounds of formula (I) wherein R$^{1a}$ represents all R$^1$ substituents other than C$_{1-4}$alkyl substituted with amino; or

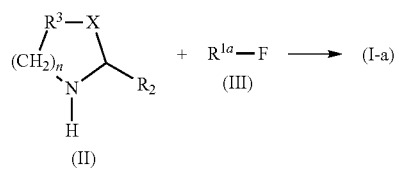

b) an intermediate of formula (II) is reacted with an intermediate of formula (IV), thereby yielding a compound of formula (I-a);

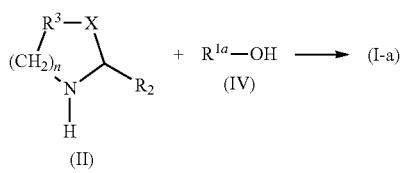

wherein in the above reaction schemes the radicals $R^1$, $R^2$, $R^3$, and the integer n, are as defined in claim 1.

7. A method of treating an eating disorder, obesity, a psychotic syndrome or an associated psychiatric disorder comprising administering an effective amount of a compound of Formula I as claimed in claim 1 to a warm blooded animal in need of such treatment.

8. The method of claim 7, wherein the warm blooded animal is a human.

* * * * *